US010442866B1

(12) United States Patent
Hu et al.

(10) Patent No.: US 10,442,866 B1
(45) Date of Patent: Oct. 15, 2019

(54) ANTIBODIES BINDING OX40 AND USES THEREOF

(71) Applicant: Beijing Mabworks Biotech Co. Ltd, Beijing (CN)

(72) Inventors: Wenqi Hu, Las Vegas, NV (US); Jiangmei Li, Beijing (CN); Lun Jiang, Beijing (CN); Feng Li, Beijing (CN)

(73) Assignee: Beijing Mabworks Biotech Co. Ltd, Beijing (CN)

( * ) Notice: Subject to any disclaimer, the term of this patent is extended or adjusted under 35 U.S.C. 154(b) by 0 days.

(21) Appl. No.: 16/254,624

(22) Filed: Jan. 23, 2019

(51) Int. Cl.
| | |
|---|---|
| *A61K 39/395* | (2006.01) |
| *C07K 16/00* | (2006.01) |
| *C07K 16/46* | (2006.01) |
| *C07K 16/28* | (2006.01) |
| *A61K 35/00* | (2006.01) |
| *A61K 31/7115* | (2006.01) |
| *A61K 39/00* | (2006.01) |
| *A61K 31/282* | (2006.01) |

(52) U.S. Cl.
CPC ........ *C07K 16/2878* (2013.01); *A61K 31/282* (2013.01); *A61K 31/7115* (2013.01); *A61K 35/00* (2013.01); *A61K 39/001118* (2018.08); *C07K 16/2818* (2013.01); *C07K 16/2827* (2013.01); *A61K 2039/55533* (2013.01); *A61K 2039/55561* (2013.01)

(58) Field of Classification Search
None
See application file for complete search history.

(56) References Cited

U.S. PATENT DOCUMENTS

2016/0137740 A1    5/2016  Hammond et al.

FOREIGN PATENT DOCUMENTS

WO    WO2015/153513 A1    8/2015

OTHER PUBLICATIONS

Brown et al. Tolerance of single, but not multiple, amino acid replacements in antibody VH CDR 2: a means of minimizing B cell wastage from somatic hypermutation? J. Immuno. May 1996, 3285-91. (Year: 1996).*
Vajdos et al. Comprehensive functional maps of the antigen-binding site of an anti-ErbB2 antibody obtained with shotgun scanning mutagenesis. J. Mol. Biol., Jul 5, 2002 320(2):415-28. (Year: 2002).*
Paul, Fundamental Immunology, 3rd Edition, 1993, pp. 292-295. (Year: 1993).*
Rudikoff et al Single amino acid substitution altering antigen-binding specificity. Proc Natl Acad Sci U S A. Mar. 1982;79(6):1979-83 (Year: 1982).*
Kjaergaard et al, (2000) Therapeutic Efficacy of OX-40 Receptor Antibody Depends on Tumor Immunogenicity and Anatomic Site of Tumor Growth. Cancer Res 60(19): 5514-5521.
Linch et al., (2015) OX40 agonists and combination immunotherapy: putting the pedal to the metal. Front Oncol 5: 34.
Piconese et al, (2010) A non-redundant role for OX40 in the competitive fitness of Treg in response to IL-2. Eur J Immunol 40: 2902-2913.
Piconese et al., (2014) Human OX40 tunes the function of regulatory T cells in tumor and non-tumor areas of HCV-infected liver tissue. Hepatology 60(5): 1494-1507.
Redmond et al., (2009) The role of OX40-mediated co-stimulation in T cell activation and survival. Crit Rev Immunol 29(3): 187-201.
Ruby et al., (2009) OX40 Agonists can drive Treg expansion if the cytokine milieu is right. J Immunol 183(B): 4853-4857.
Voo et al., (2013) Antibodies targeting human OX40 expand effector T cells and block inducible and natural regulatory T cell function. Immunol. 191 (7): 3641-3650.
Webb et al., (2016) OX40, OX40L and Autoimmunity: A Comprehensive Review. Clin Rev Allergy Immunol 50(3): 312-332.
Weinberg et al., (1998), OX-40: life beyond the effector T cell stage, Semin Immunol 10(6): 471-480.
Willoughby et al., (2017) OX40: Structure and function—What questions remain? Mol Immunol 83:13-22.
Aspeslagh et al, (2018) Rationale for anti-OX40 cancer immunotherapy, Eur J Cancer 52: 50-66.
Bell et al., (2016) OX40 signaling in head and neck squamous cell carcinoma: Overcoming immunosuppression in the tumor microenvironment, Oral Oncol 52 1-10.
Boettler et al, (2012) OX40 Facilitates Control of a Persistent Virus Infection, PLoS Pathog. 8(9): e1002913.
Colombo et al, (2017), On OX40 and PD-1 Combination: Why Should OX40 Be First in Sequence? Clin Cancer Res, 23(20) 5999-6001.
Croft et al, (2003) Costimulation of T cells by OX40, 4-1BB, and CD27, Cytokine Growth Factor Rev, 14 (3-4): 265-273.
Curti et al., (2013) OX40 Is a Potent Immune-Stimulating Target in Late-Stage Cancer Patients, Cancer Res 73(24): 7189-7198.
Foote et al, (2017) A STING Agonist Given with OX40 Receptor and PD-L1 Modulators Primes Immunity and Reduces Tumor Growth in Tolerized Mice, Cancer Immunol Res 5(6):468-479.

(Continued)

*Primary Examiner* — Maher M Haddad
(74) *Attorney, Agent, or Firm* — Vicki Norton; Duane Morris LLP

(57) ABSTRACT

An isolated monoclonal antibody that specifically binds human OX40. A nucleic acid molecule encoding the antibody, an expression vector, a host cell and a method for expressing the antibody are also provided. The present invention further provides an immunoconjugate, a bispecific molecule, a chimeric antigen receptor, an oncolytic virus and a pharmaceutical composition comprising the antibody, as well as a treatment method using an anti-OX40 antibody of the invention.

19 Claims, 9 Drawing Sheets

Specification includes a Sequence Listing.

(56) References Cited

OTHER PUBLICATIONS

Jahan et al., (2018) Agonist OX40 immunotherapy improves survival in glioma-bearing mice and is complementary with vaccination with irradiated GM-CSF-expressing tumor cells. Neuro Oncol. 10;20(1): 44-54.

Jensen et al., (2010) Signaling through OX40 Enhances Anti-tumor Immunity. Semin. Oncol. 37(5): 524-532.

\* cited by examiner

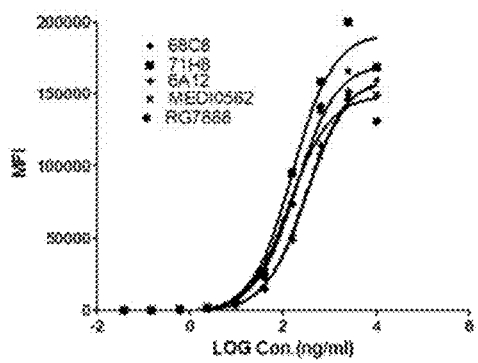
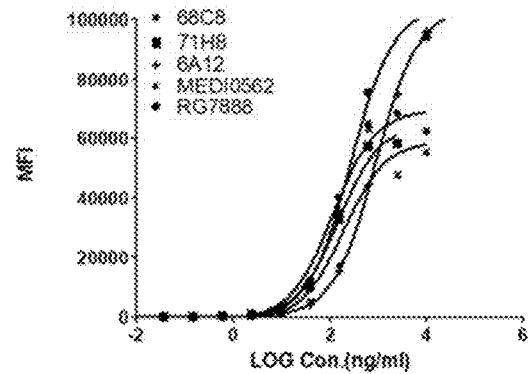
FIG. 5A  FIG. 5B
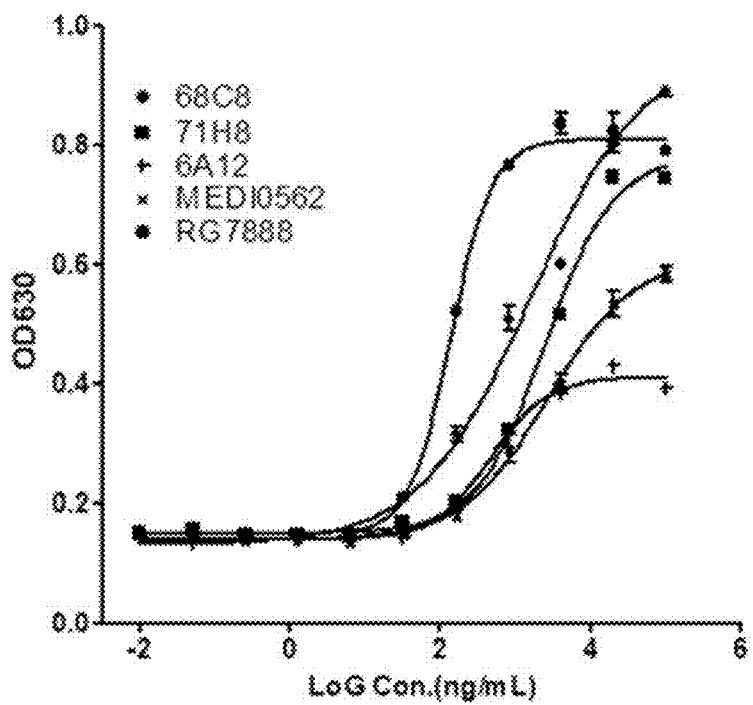
FIG. 6

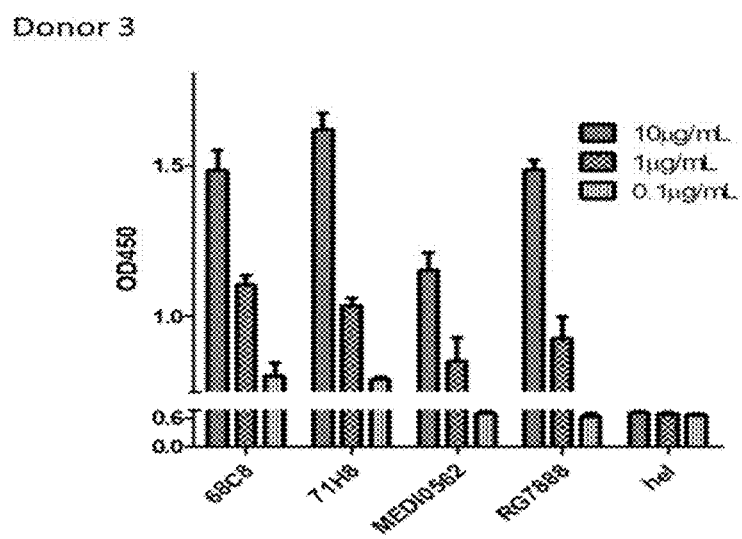
FIG. 7
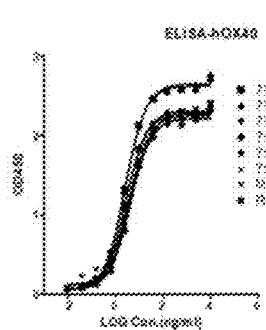 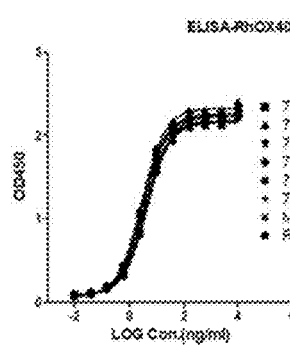 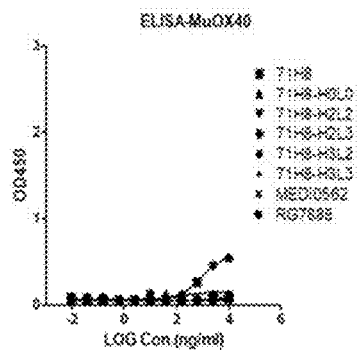
FIG. 8A     FIG. 8B     FIG. 8C
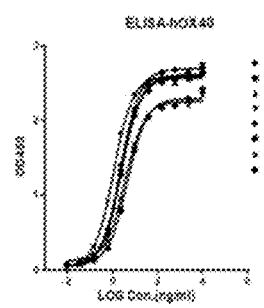 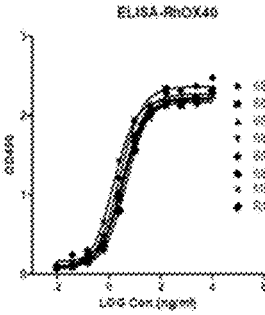 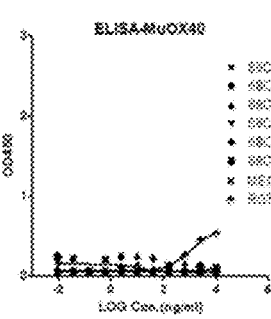
FIG. 8D     FIG. 8E     FIG. 8F

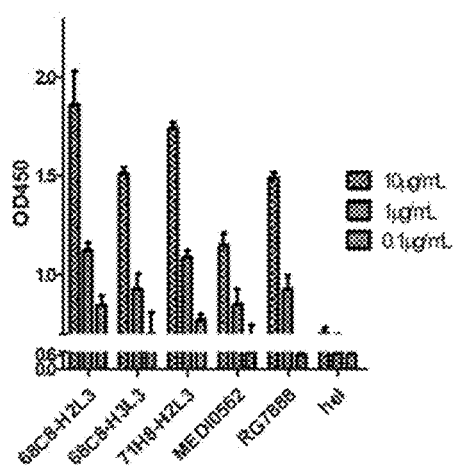
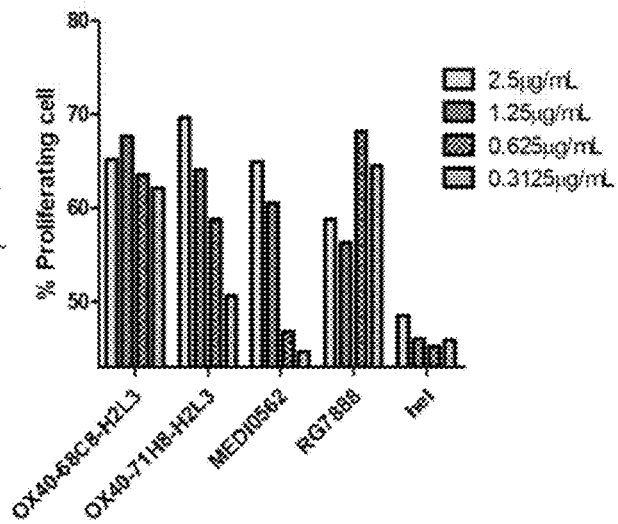
FIG. 11A  FIG. 11B
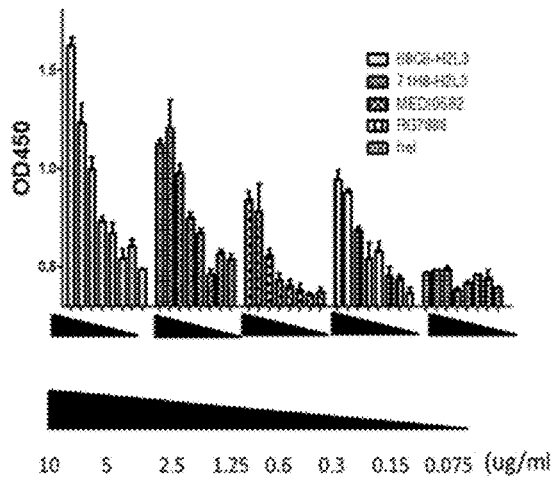
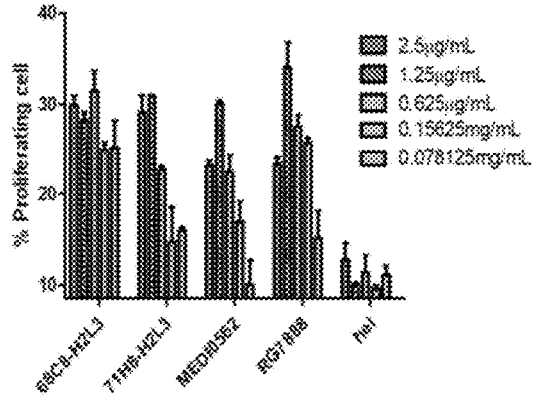
FIG. 12A  FIG. 12B

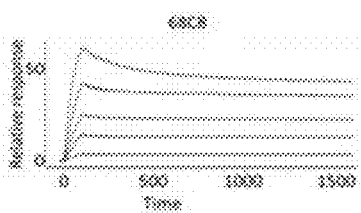 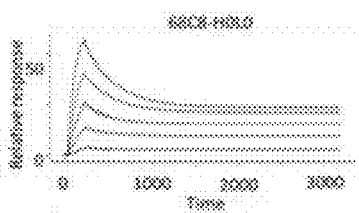 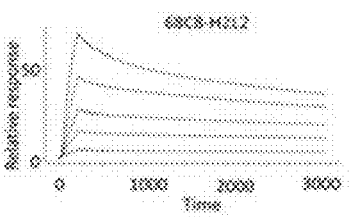
FIG. 13A  FIG. 13B  FIG. 13C
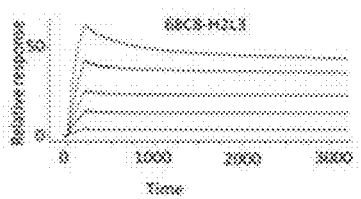 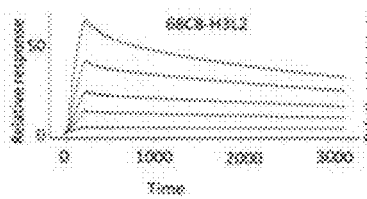 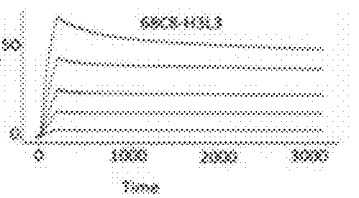
FIG. 13D  FIG. 13E  FIG. 13F
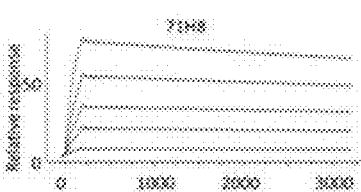 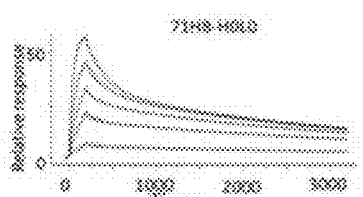 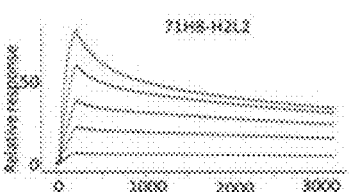
FIG. 13G  FIG. 13H  FIG. 13I
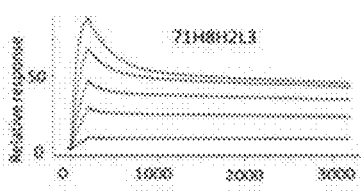 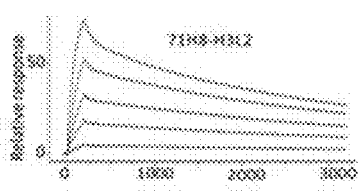 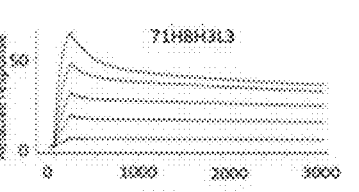
FIG. 13J  FIG. 13K  FIG. 13L
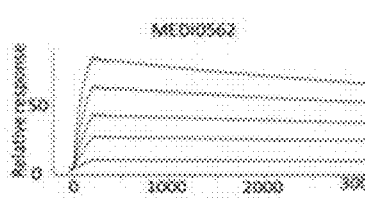 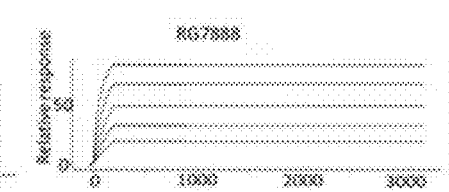
FIG. 13M  FIG. 13N

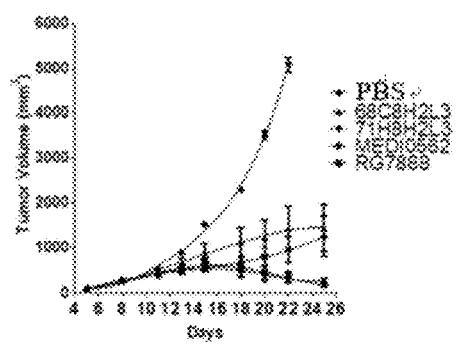
FIG. 16A
FIG. 16B  FIG. 16C  FIG. 16D
FIG. 16E  FIG. 16F
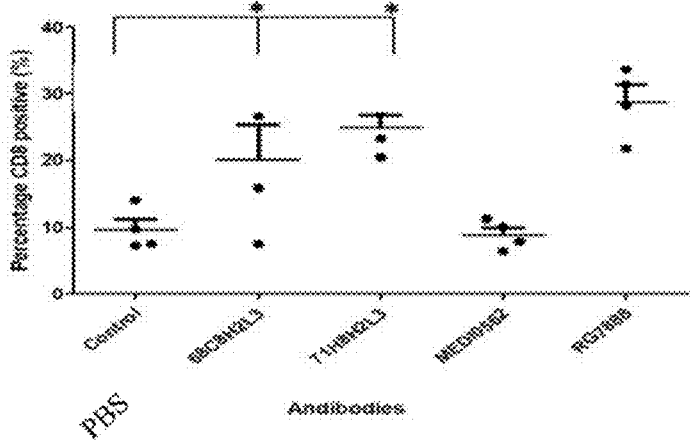
FIG. 17

ANTIBODIES BINDING OX40 AND USES THEREOF

FIELD OF THE INVENTION

The invention relates to an antibody specifically binding to human OX40, preparation and use thereof, especially its use in treatment of diseases associated with OX40, such as cancers and infectious diseases.

BACKGROUND OF THE INVENTION

The T cell costimulatory receptor, OX40, also known as CD134, TNFRSF4 and ACT35, is a member of the tumor necrosis factor receptor superfamily. It is involved in potentiating T cell responses triggered through TCRs, and expressed primarily on activated T cells, including CD4+ T cells, CD8+ T cells and regulatory T-cells (Tregs) (Redmond et al., (2009) Crit. Rev. Immunol. 29(3): 187-201; Jensen et al., (2010) Semin. Oncol. 37(5):524-532). Unlike CD 28, OX40 is not expressed on naïve T cells. Its expression peaks between 12 hours and 5-6 days post antigen stimulation. Its ligand OX40L, in a similar manner, is induced and detected on the surface of antigen presenting cells 1 to 3 days after antigen encounter (Willoughby et al., (2017) Mol Immunol 83: 13-22).

Upon binding to OX40L, OX40 signaling was reported to increase cytokine production and enhance CD4+ and CD8+ T cell proliferation and survival (Weinberg et al., (1998), Semin Immunol 10(6): 471-480; Kjaergaard et al., (2000) Cancer Res 60(19): 5514-5521; Willoughby et al., supra; Croft et al., (2003) Cytokine Growth Factor Rev. 14 (3-4): 265-273). In vivo studies showed that OX40 receptor engagement by OX40L improved tumor-free survival in mice bearing tumors such as lymphoma, melanoma, sarcoma, colon cancer, breast cancer and glioma ((Aspeslagh et al., (2016) Eur J Cancer 52: 50-66; Bell et al. (2016) Oral Oncol 52: 1-10; Webb et al., (2016) Clin Rev Allergy Immunol 50(3): 312-332; Willoughby et al., supra).

OX40 also plays an important role in Treg development and function. OX40 signaling in some contexts boosted Treg fitness and proliferation, and OX40+ Tregs were found at tumor sites at higher levels (Piconese et al., (2014) Hepatology 60(5):1494-1507; Ruby et al., (2009) J Immunol 183: 4853-4857; Piconese et al., (2010) Eur J Immunol 40: 2902-2913). However, high doses of agonistic anti-OX40 antibodies were shown to successfully block Treg mediated suppression by reducing Treg viability via an apparently apoptotic process (Voo et al., (2013) Immunol. 191 (7): 3641-3650).

With its role in immune response as described above, OX40 has been identified as a potential target for immunotherapy. Agonistic anti-OX40 antibodies that activate OX40 signaling have been used in preclinical studies to treat tumors and infectious diseases (Boettler et al., (2012) PLoS Pathog. 8(9): e1002913; Jahan et al., (2018) Neuro Oncol. 10; 20(1):44-54), while antagonistic antibodies which block OX40 signaling may be used to treat autoimmune or inflammatory diseases. In a first-in-human phase I clinical trial using a murine IgG1, anti-OX40 monoclonal agonistic antibody, 12 out of 30 patients having metastatic solid malignancies showed evidence of tumor regression after just one cycle of treatment (Curti et al. (2013) Cancer Res 73(24): 7189-7198). Anti-OX40 monotherapy has been further studied in combination with other monoclonal antibodies, chemotherapy and cytokines to improve therapeutic effects (Linch, McNamara et al. (2015) Front Oncol 5: 34; Colombo et al., (2017), Clin Cancer Res 23(20): 5999-6001; Foote et al., (2017) Cancer Immunol Res 5(6): 468-479).

Despite the insight into the structural basis of the OX40-OX40L interaction, what determines whether an antibody is an agonistic or antagonistic antibody against OX40 is not yet clear. There remains a need for more OX40 antibodies with desirable pharmaceutical characteristics.

SUMMARY OF THE INVENTION

The present invention provides an isolated monoclonal antibody, for example, a mouse, human, chimeric or humanized monoclonal antibody, that binds to OX40 (e.g., the human OX40, and monkey OX40). It may be an agonistic OX40 antibody that activates OX40 signaling.

The antibody of the invention can be used for a variety of applications, including detection of the OX40 protein, and treatment and prevention of OX40 associated diseases, such as cancers and infectious diseases.

Accordingly, in one aspect, the invention pertains to an isolated monoclonal antibody (e.g., a humanized antibody), or an antigen-binding portion thereof, that binds OX40, having a heavy chain variable region that comprises a CDR1 region, a CDR2 region and a CDR3 region, wherein the CDR1 region, the CDR2 region and the CDR3 region comprise amino acid sequences having at least 80%, 85%, 90%, 95%, 98%, or 99% identity to, or set forth in
 (1) SEQ ID NOs: 1, 3 and 6, respectively;
 (2) SEQ ID NOs: 1, 4 and 6, respectively; or
 (3) SEQ ID NOs: 2, 5 and 7, respectively;
wherein, the antibody, or antigen-binding fragment thereof, binds to OX40.

In one aspect, an isolated monoclonal antibody, or an antigen-binding portion thereof, of the present invention comprises a heavy chain variable region comprising an amino acid sequence having at least 80%, 85%, 90%, 95%, 98% or 99% identity to, or set forth in SEQ ID NOs: 14, 15, 16, 17, 18, 19, 20, 21 or 22, wherein the antibody or antigen-binding fragment thereof binds to OX40.

In one aspect, an isolated monoclonal antibody, or an antigen-binding portion thereof, of the present invention comprises a light chain variable region that comprises a CDR1 region, a CDR2 region and a CDR3 region, wherein the CDR1 region, the CDR2 region, and the CDR3 region comprise amino acid sequences having at least 80%, 85%, 90%, 95%, 98% or 99% identity to, or set forth in
 (1) SEQ ID NOs: 8, 10 and 12, respectively; or
 (2) SEQ ID NOs: 9, 11 and 13, respectively;
wherein the antibody or antigen-binding fragment thereof binds to OX40.

In one aspect, an isolated monoclonal antibody, or an antigen-binding portion thereof, of the present invention comprises a light chain variable region comprising an amino acid sequence having at least 80%, 85%, 90%, 95%, 98% or 99% identity to, or set forth in SEQ ID NOs: 23, 24, 25, 26, 27 or 28, wherein the antibody or antigen-binding fragment thereof binds to OX40.

In one aspect, an isolated monoclonal antibody, or an antigen-binding portion thereof, of the present invention comprises a heavy chain variable region and a light chain variable region each comprises a CDR1 region, a CDR2 region and a CDR3 region, wherein the heavy chain variable region CDR1, CDR2 and CDR3, and the light chain variable region CDR1, CDR2 and CDR3 comprise amino acid sequences having at least 80%, 85%, 90%, 95%, 98% or 99% identity to, or set forth in (1) SEQ ID NOs: 1, 3, 6, 8, 10 and 12, respectively; (2) SEQ ID NOs: 1, 4, 6, 8, 10 and 12, respectively; or (3) 2, 5, 7, 9, 11 and 13, respectively, wherein the antibody or antigen-binding fragment thereof binds to OX40.

In one embodiment, an isolated monoclonal antibody, or the antigen-binding portion thereof, of the present invention comprises a heavy chain variable region and a light chain variable region, the heavy chain variable region and the light chain variable region comprising amino acid sequences having at least 80%, 85%, 90%, 95%, 98% or 99% identity to, or set forth in (1) SEQ ID NOs: 14 and 23, respectively; (2) SEQ ID NOs: 15 and 24, respectively; (3) SEQ ID NOs: 16 and 25, respectively; (4) SEQ ID NOs: 17 and 26, respectively; (5) SEQ ID NOs: 18 and 27, respectively; (6) SEQ ID NOs: 18 and 28, respectively; (7) SEQ ID NOs: 19 and 27, respectively; (8) SEQ ID NOs: 19 and 28, respectively; (9) SEQ ID NOs: 20 and 26, respectively; (10) SEQ ID NOs: 21 and 27, respectively; (11) SEQ ID NOs: 21 and 28, respectively; (12) SEQ ID NOs: 22 and 27, respectively; or (13) SEQ ID NOs: 22 and 28, respectively, wherein the antibody or antigen-binding fragment thereof binds to OX40.

In one embodiment, an isolated monoclonal antibody, or the antigen-binding portion thereof, of the present invention comprises a heavy chain and a light chain, the heavy chain comprising a heavy chain variable region and a heavy chain constant region, the light chain comprising a light chain variable region and a light chain constant region, wherein, the heavy chain constant region and the light chain constant region comprise amino acid sequences having at least 80%, 85%, 90%, 95%, 98% or 99% identity to, or set forth in SEQ ID Nos: 29 and 30, respectively, and the heavy chain variable region and the light chain variable region comprise amino acid sequences described above, wherein the antibody or antigen-binding fragment thereof binds to OX40.

The antibody of the present invention in some embodiments comprises or consists of two heavy chains and two light chains, wherein each heavy chain comprises the heavy chain constant region, heavy chain variable region or CDR sequences mentioned above, and each light chain comprises the light chain constant region, light chain variable region or CDR sequences mentioned above, wherein the antibody binds to OX40. The antibody of the invention can be a full-length antibody, for example, of an IgG1, IgG2 or IgG4 isotype, The antibody of the present invention in other embodiments may be a single chain antibody, or consists of antibody fragments, such as Fab or Fab'2 fragments.

The antibody, or antigen-binding fragment, of the present invention binds specifically to human and monkey OX40, and blocks OX40-OX40L interaction. It is an agonistic OX40 antibody, activating OX40 signaling and promoting T cell costimulation and accordingly IL-2 secretion and T cell proliferaiton. The antibody or antigen-binding fragment of the present invention has an in vivo anti-tumor effect comparable to or better than prior art OX40 antibodies.

The invention also provides an immunoconjugate comprising an antibody of the invention, or antigen-binding portion thereof, linked to a therapeutic agent, such as a cytotoxin. The invention also provides a bispecific molecule comprising an antibody, or antigen-binding portion thereof, of the invention, linked to a second functional moiety (e.g., a second antibody) having a different binding specificity than said antibody, or antigen-binding portion thereof. In another aspect, the antibody or an antigen binding portions thereof of the present invention can be made into part of a chimeric antigen receptor (CAR). The antibody or an antigen binding portions thereof of the present invention can also be encoded by or used in conjunction with an oncolytic virus.

Compositions comprising an antibody, or antigen-binding portion thereof, or immunoconjugate or bispecific molecule of the invention, and a pharmaceutically acceptable carrier, are also provided.

Nucleic acid molecules encoding the antibodies, or antigen-binding portions thereof, of the invention are also encompassed by the invention, as well as expression vectors comprising such nucleic acids and host cells comprising such expression vectors. A method for preparing an anti-OX40 antibody using the host cell comprising the expression vector is also provided, comprising steps of (i) expressing the antibody in the host cell and (ii) isolating the antibody from the host cell or its cell culture.

In another aspect, the invention provides a method for enhancing an immune response in a subject, comprising administering to the subject a therapeutically effective amount of the antibody, or antigen-binding portion thereof, of the invention. In some embodiments, the method comprises administering a composition, a bispecific molecule, an immunnoconjugate, a CAR-T cell, or an antibody-encoding or antibody-bearing oncolytic virus of the invention.

In another aspect, the invention provides a method for treating an infectious disease in a subject, comprising administering to the subject a therapeutically effective amount of the antibody, or antigen-binding portion thereof, of the invention. In some embodiments, the method comprises administering a composition, a bispecific molecule, an immunnoconjugate, a CAR-T cell, or an antibody-encoding or antibody-bearing oncolytic virus of the invention. In some embodiments, additional anti-infective agents can be administered with the antibody, or an antigen-binding portion thereof, of the invention, such as antibacterial, antiviral, antifungal, and antiparasitic agents.

In yet another aspect, the invention provides a method for preventing, treating or ameliorating a cancer disease in a subject, comprising administering to the subject a therapeutically effective amount of the antibody, or antigen-binding portion thereof, of the invention. The cancer may be a solid or non-solid tumor, including, but not limited to, lymphoma, melanoma, sarcoma, colon cancer, breast cancer, glioma, head and neck squamous cell carcinoma, non-small cell lung cancer, and colon adenocarcinoma. In some embodiments, the method comprises administering a composition, a bispecific molecule, an immunnoconjugate, a CAR-T cell, or an antibody-encoding or antibody-bearing oncolytic virus of the invention. In some embodiments, at least one additional anti-cancer antibody can be administered with the antibody, or an antigen-binding portion thereof, of the invention, such as an anti-PD-1 antibody, an anti-PD-L1 antibody, an anti-LAG-3 antibody and/or an anti-CTLA-4 antibody. In yet another embodiment, an antibody, or an antigen-binding portion thereof, of the invention is administered with a cytokine (e.g., IL-2 and/or IL-21), or a costimulatory antibody (e.g., an anti-CD137 and/or anti-GITR antibody). In another embodiment, an antibody, or an antigen-binding portion thereof, of the invention is administered with a chemotherapeutic agent, which may be a cytotoxic agent, such as epirubicin, oxaliplatin, and/or 5-fluorouracil (5-FU). The antibodies of the present invention can be, for example, mouse, human, chimeric or humanized antibodies.

In one embodiment, the cancer disease treatment method of the invention further comprises administering an agent activating OX40 expression. Expression of OX40 is preferably at the cell surface of T cells. The agent can be a TLR9 ligand, or specifically an unmethylated CpG oligonucleotide. Alternatively, the agent can be phytohemagglutinin-leucoagglutinin, or IL-2.

Other features and advantages of the instant disclosure will be apparent from the following detailed description and examples, which should not be construed as limiting. The contents of all references, Genbank entries, patents and published patent applications cited throughout this application are expressly incorporated herein by reference.

BRIEF DESCRIPTION OF THE DRAWINGS

FIGS. 5A and 5B show the binding capacity of the chimeric anti-OX40 antibodies to human OX 40 (A) or monkey OX40 (B) expressed on HEK293A cells.

FIG. 6 shows the agonistic activity of the chimeric anti-OX40 antibodies.

FIG. 7 shows the effect of chimeric anti-OX40 antibodies on T cell costimulation where PBMCs were obtained from Donor 3.

FIG. 8A-8F show the binding capacity of humanized anti-OX40 antibodies to human, monkey or mouse OX40. Antibody 71H8 and its humanized versions bound to human (A) and monkey OX 40 (B) but not to mouse OX40 (C), and antibody 68C8 and its humanized versions bound to human (D) and monkey OX40 (E) but not to mouse OX40 (F).

FIGS. 11A and 11B show that the effect of humanized anti-OX40 antibodies on IL-2 secretion (A) and CD4+ T cell proliferation (B) using PBMCs from Donor 4.

FIGS. 12A and 12B show that the effect of humanized anti-OX40 Antibodies on IL-2 secretion (A) and CD4+ T cell proliferation (B) using PBMCs from Donor 5.

FIG. 13A-13N show the binding affinity of anti-OX40 antibodies 68C8 (A), 68C8-H0L0 (B), 68C8-H2L2 (C), 68C8-H2L3 (D), 68C8-H3L2 (E), 68C8-H3L3 (F), 71H8 (G), 71H8-H0L0 (H), 71H8-H2L2 (I), 71H8-H2L3 (J), 71H8-H3L2 (K), 71H8-H3L3 (L), MEDI0562 (M) and RG7888 (N) to human OX40 measured by SPR.

FIG. 16A-16F show the group average tumor volumes (A) and individual tumor volumes in groups administered with PBS (B), humanized anti-OX40 antibodies 68C8-H2L3 (C) and 71H8-H2L3 (D), MEDI0562 (E) and RG7888 (F), indicating in vivo inhibitory effect of anti-OX40 antibodies on tumor growth.

FIG. 17 shows the in vivo effect of humanized anti-OX40 antibodies on tumor infiltrating CD8+ T cell proliferation.

DETAILED DESCRIPTION OF THE INVENTION

Figure 1:
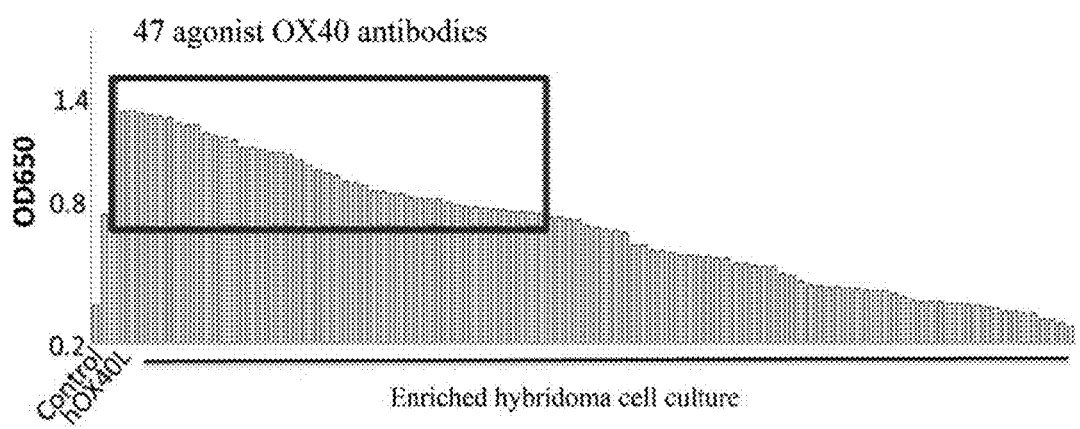
FIG. 1 shows the agonistic activity ranking of 84 hybridoma clones.

To ensure that the present disclosure may be more readily understood, certain terms are first defined. Additional definitions are set forth throughout the detailed description.

The term "OX40" refers to tumor necrosis factor receptor superfamily, member 4. The term "OX40" comprises variants, isoforms, homologs, orthologs and paralogs. For example, an antibody specific for a human OX40 protein may, in certain cases, cross-react with an OX40 protein from a species other than human, such as monkey. In other embodiments, an antibody specific for a human OX40 protein may be completely specific for the human OX40 protein and exhibit no cross-reactivity to other species or of other types, or may cross-react with OX40 from certain other species but not all other species.

The term "human OX40" refers to an OX40 protein having an amino acid sequence from a human, such as the amino acid sequence of human OX40 having a Genbank accession number of NP 003318 (SEQ ID NO.:32). The terms "monkey or rhesus OX40" and "mouse OX40" refer to monkey and mouse OX40 sequences, respectively, e.g. those with the amino acid sequences having Genbank Accession Nos. NP_001090870 (SEQ ID NO.:34) and NP_035789 (SEQ ID NO.:36), respectively.

The term "antibody" as referred to herein includes whole antibodies and any antigen binding fragment (i.e., "antigen-binding portion") or single chains thereof. Whole antibodies are glycoproteins comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, $C_{H1}$, $C_{H2}$ and $C_{H3}$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system.

The term "antigen-binding portion" of an antibody (or simply "antibody portion"), as used herein, refers to one or more fragments of an antibody that retain the ability to specifically bind to an antigen (e.g., a OX40 protein). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_{H1}$ and $C_{H1}$ domains; (iv) a Fv fragment consisting of the $V_L$ and $V_H$ domains of a single arm of an antibody, (v) a dAb fragment (Ward et al., (1989) *Nature* 341:544-546), which consists of a $V_H$ domain; (vi) an isolated complementarity determining region (CDR); and (viii) a nanobody, a heavy chain variable region containing a single variable domain and two constant domains. Furthermore, although the two domains of the Fv fragment, $V_L$ and $V_H$, are coded by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al., (1988) *Science* 242:423-426; and Huston et al., (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

An "isolated antibody", as used herein, is intended to refer to an antibody that is substantially free of other antibodies having different antigenic specificities (e.g., an isolated antibody that specifically binds a OX40 protein is substantially free of antibodies that specifically bind antigens other than OX40 proteins). An isolated antibody that specifically binds a human OX40 protein may, however, have cross-reactivity to other antigens, such as OX40 proteins from other species. Moreover, an isolated antibody can be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "mouse antibody", as used herein, is intended to include antibodies having variable regions in which both the framework and CDR regions are derived from mouse germline immunoglobulin sequences. Furthermore, if the antibody contains a constant region, the constant region also is derived from mouse germline immunoglobulin sequences. The mouse antibodies of the invention can include amino acid residues not encoded by mouse germline immunoglobulin sequences (e.g., mutations introduced by random or site-specific mutagenesis in vitro or by somatic mutation in vivo). However, the term "mouse antibody", as used herein, is not intended to include antibodies in which CDR sequences derived from the germline of another mammalian species have been grafted onto mouse framework sequences.

The term "chimeric antibody" refers to an antibody made by combining genetic material from a nonhuman source with genetic material from a human being. Or more generally, a chimetic antibody is an antibody having genetic material from a certain species with genetic material from another species.

The term "humanized antibody", as used herein, refers to an antibody from non-human species whose protein sequences have been modified to increase similarity to antibody variants produced naturally in humans.

The phrases "an antibody recognizing an antigen" and "an antibody specific for an antigen" are used interchangeably herein with the term "an antibody which binds specifically to an antigen."

As used herein, an antibody that "specifically binds to human OX40" is intended to refer to an antibody that binds to human OX40 protein (and possibly a OX40 protein from one or more non-human species) but does not substantially bind to non-OX40 proteins. Preferably, the antibody binds to human OX40 protein with "high affinity", namely with a $K_D$ of $5.0 \times 10^{-8}$ M or less, more preferably $1.0 \times 10^{-8}$ M or less, and more preferably $5.0 \times 10^{-9}$ M or less.

The term "does not substantially bind" to a protein or cells, as used herein, means does not bind or does not bind with a high affinity to the protein or cells, i.e. binds to the protein or cells with a $K_D$ of $1.0 \times 10^{-6}$ M or more, more preferably $1.0 \times 10^{-5}$ M or more, more preferably $1.0 \times 10^{-4}$ M or more, more preferably $1.0 \times 10^{-3}$ M or more, even more preferably $1.0 \times 10^{-2}$ M or more.

The term "high affinity" for an IgG antibody refers to an antibody having a $K_D$ of $1.0 \times 10^{-6}$ M or less, more preferably $5.0 \times 10^{-8}$ M or less, even more preferably $1.0 \times 10^{-9}$ M or less, even more preferably $5.0 \times 10^{-9}$ M or less and even more preferably $1.0 \times 10^{-9}$ M or less for a target antigen. However, "high affinity" binding can vary for other antibody isotypes. For example, "high affinity" binding for an IgM isotype refers to an antibody having a $K_D$ of $10^{-6}$ M or less, more preferably $10^{-7}$ M or less, even more preferably $10^{-8}$ M or less.

The term "Kassoc" or "$K_a$", as used herein, is intended to refer to the association rate of a particular antibody-antigen interaction, whereas the term "$K_{dis}$" or "$K_d$", as used herein, is intended to refer to the dissociation rate of a particular antibody-antigen interaction. The term "$K_D$", as used herein, is intended to refer to the dissociation constant, which is obtained from the ratio of $K_d$ to $K_a$ (i.e., $K_d/K_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a Biacore™ system.

The term "$EC_{50}$", also known as half maximal effective concentration, refers to the concentration of an antibody which induces a response halfway between the baseline and maximum after a specified exposure time.

The term "subject" includes any human or nonhuman animal. The term "nonhuman animal" includes all vertebrates, e.g., mammals and non-mammals, such as non-human primates, sheep, dogs, cats, cows, horses, chickens, amphibians, and reptiles, although mammals are preferred, such as non-human primates, sheep, dogs, cats, cows and horses.

The term "agonistic OX40 antibody" or "agonistic anti-OX40 antibody" refers to an anti-OX40 antibody that binds to OX40 and activates or induces OX40 signaling to promote T cell proliferation and survival. While the term "antagonistic OX40 antibody" refers to an anti-OX40 antibody that blocks OX40 signaling, thereby remedy hyperactive T cell pathologies, and can be used to treat, e.g, asthma, colitis and arthritis.

The term "therapeutically effective amount" means an amount of the antibody of the present invention sufficient to prevent or ameliorate the symptoms associated with a disease or condition (such as a cancer) and/or lessen the severity of the disease or condition. A therapeutically effective amount is understood to be in context to the condition being treated, where the actual effective amount is readily discerned by those of skill in the art.

Various aspects of the invention are described in further detail in the following subsections.

Anti-OX40 Antibodies Having Binding Specificity to Human OX40 and Advantageous Functional Properties Antibodies of the invention specifically bind to human OX40 with high affinity, e.g., with a $K_D$ of $1 \times 10^{-8}$ M or less.

The antibodies also have cross-reactivity with monkey OX40, but do not bind to mouse OX40.

The antibodies of the invention are agonistic OX40 antibodies that activate or induce OX40 signaling and involve in T cell costimulation, promoting IL-2 secretion and CD8+ T cell proliferation.

The antibodies of the invention have good in vivo anti-tumor effects. Tumor would not grow or even totally vanish post antibody withhold.

Preferred antibodies of the invention are monoclonal antibodies. Additionally or alternatively, the antibodies can be, for example, mouse, chimeric or humanized monoclonal antibodies.

Monoclonal Anti-OX40 Antibody

A preferred antibody of the invention is the monoclonal antibody structurally and chemically characterized as described below and in the following Examples. The $V_H$ amino acid sequence of the anti-OX40 antibody is set forth in SEQ ID NOs: 14, 15, 16, 17, 18, 19, 20, 21 or 22. The $V_L$ amino acid sequence of the anti-OX40 antibody is shown in SEQ ID NOs: 23, 24, 25, 26, 27 or 28. The amino acid sequences of the heavy/light chain variable regions of the antibodies are summarized in Table 1 below, some clones sharing the same $V_H$ or $V_L$. Preferable amino acid sequences of the heavy chain constant region and the light chain constant region for all clones are set forth in SEQ ID NOs: 29 and 30, respectively.

(a) the CDR1, CDR2, and CDR3 regions of the heavy chain variable region listed above in Table 1; and
(b) the CDR1, CDR2, and CDR3 regions of the light chain variable region listed above in Table 1 or the CDRs of another anti-OX40 antibody, wherein the antibody specifically binds human OX40.

In yet another embodiment, the antibody, or antigen binding portion thereof, includes the heavy chain variable CDR2 region of anti-OX40 antibody combined with CDRs of other antibodies which bind human OX40, e.g., CDR1 and/or CDR3 from the heavy chain variable region, and/or CDR1, CDR2, and/or CDR3 from the light chain variable region of a different anti-OX40 antibody.

In addition, it is well known in the art that the CDR3 domain, independently from the CDR1 and/or CDR2 domain(s), alone can determine the binding specificity of an antibody for a cognate antigen and that multiple antibodies can predictably be generated having the same binding specificity based on a common CDR3 sequence. See, e.g., Klimka et al., *British J. of Cancer* 83(2):252-260 (2000); Beiboer et al. *J. Mol. Biol.* 296:833-849 (2000); Rader et al., *Proc. Natl. Acad. Sci. U.S.A.* 95:8910-8915 (1998); Barbas et al., *J. Am. Chem. Soc.* 116:2161-2162 (1994); Barbas et al., *Proc. Natl. Acad. Sci. U.S.A.* 92:2529-2533 (1995); Ditzel et al., *J. Immunol.* 157:739-749 (1996); Berezov et al., *BIAjournal 8: Scientific Review* 8 (2001); Igarashi et al., *J Biochem* (Tokyo) 117:452-7 (1995); Bourgeois et al., *J Virol* 72:807-10

TABLE 1

Amino acid sequences of heavy/light chain variable regions

| Clone/SEQ ID NO. | HV-CDR1 | HV-CDR2 | HV-CDR3 | HV | LV-CDR1 | LV-CDR2 | LV-CDR3 | LV |
|---|---|---|---|---|---|---|---|---|
| 71H8 | 1 | 3 | 6 | 14 | 8 | 10 | 12 | 23 |
| 68C8 | 1 | 4 | 6 | 15 | 8 | 10 | 12 | 24 |
| 6A12 | 2 | 5 | 7 | 16 | 9 | 11 | 13 | 25 |
| 68C8-VH0VL0 | 1 | 4 | 6 | 17 | 8 | 10 | 12 | 26 |
| 68C8-VH2VL2 | 1 | 4 | 6 | 18 | 8 | 10 | 12 | 27 |
| 68C8-VH2VL3 | 1 | 4 | 6 | 18 | 8 | 10 | 12 | 28 |
| 68C8-VH3VL2 | 1 | 4 | 6 | 19 | 8 | 10 | 12 | 27 |
| 68C8-VH3VL3 | 1 | 4 | 6 | 19 | 8 | 10 | 12 | 28 |
| 71H8-VH0VL0 | 1 | 3 | 6 | 20 | 8 | 10 | 12 | 26 |
| 71H8-VH2VL2 | 1 | 3 | 6 | 21 | 8 | 10 | 12 | 27 |
| 71H8-VH2VL3 | 1 | 3 | 6 | 21 | 8 | 10 | 12 | 28 |
| 71H8-VH3VL2 | 1 | 3 | 6 | 22 | 8 | 10 | 12 | 27 |
| 71H8-VH3VL3 | 1 | 3 | 6 | 22 | 8 | 10 | 12 | 28 |

68C8-VH0VL0, 68C8-VH2VL2, 68C8-VH2VL3, 68C8-VH3VL2, 68C8-VH3VL3, 71H8-VH0VL0, 71H8-VH2VL2, 71H8-VH2VL3, 71H8-VH3VL2 and 71H8-VH3VL3 are also referred to as 68C8-H0L0, 68C8-H2L2, 68C8-H2L3, 68C8-H3L2, 68C8-H3L3, 71H8-H0L0, 71H8-H2L2, 71H8-H2L3, 71H8-H3L2 and 71H8-H3L3, respectively.

The $V_H$ and $V_L$ sequences (or CDR sequences) of other anti-OX40 antibodies which bind to human OX40 can be "mixed and matched" with the $V_H$ and $V_L$ sequences (or CDR sequences) of the anti-OX40 antibody of the present invention. Preferably, when $V_H$ and $V_L$ chains (or the CDRs within such chains) are mixed and matched, a $V_H$ sequence from a particular $V_H/V_L$ pairing is replaced with a structurally similar $V_H$ sequence. Likewise, preferably a $V_L$ sequence from a particular $V_H/V_L$ pairing is replaced with a structurally similar $V_L$ sequence.

Accordingly, in one embodiment, an antibody of the invention, or an antigen binding portion thereof, comprises:
(a) a heavy chain variable region comprising an amino acid sequence listed above in Table 1; and
(b) a light chain variable region comprising an amino acid sequence listed above in Table 1, or the $V_L$ of another anti-OX40 antibody, wherein the antibody specifically binds human OX40.

In another embodiment, an antibody of the invention, or an antigen binding portion thereof, comprises:

(1998); Levi et al., *Proc. Natl. Acad. Sci. U.S.A.* 90:4374-8 (1993); Polymenis and Stoller, *Immunol.* 152:5218-5329 (1994) and Xu and Davis, *Immunity* 13:37-45 (2000). See also, U.S. Pat. Nos. 6,951,646; 6,914,128; 6,090,382; 6,818,216; 6,156,313; 6,827,925; 5,833,943; 5,762,905 and 5,760,185. Each of these references is hereby incorporated by reference in its entirety.

Accordingly, in another embodiment, antibodies of the invention comprise the CDR2 of the heavy chain variable region of the anti-OX40 antibody and at least the CDR3 of the heavy and/or light chain variable region of the anti-OX40 antibody, or the CDR3 of the heavy and/or light chain variable region of another anti-OX40 antibody, wherein the antibody is capable of specifically binding to human OX40. These antibodies preferably (a) compete for binding with OX40; (b) retain the functional characteristics; (c) bind to the same epitope; and/or (d) have a similar binding affinity as the anti-OX40 antibody of the present invention. In yet another embodiment, the antibodies further may comprise the CDR2 of the light chain variable region of the anti-OX40 antibody, or the CDR2 of the light chain variable region of another anti-OX40 antibody, wherein the antibody is capable of specifically binding to human OX40. In another embodiment, the antibodies of the invention may include the CDR1 of the heavy and/or light chain variable region of the anti-OX40 antibody, or the CDR1 of the heavy and/or light chain variable region of another anti-OX40 antibody, wherein the antibody is capable of specifically binding to human OX40.

Conservative Modifications

In another embodiment, an antibody of the invention comprises a heavy and/or light chain variable region sequences of CDR1, CDR2 and CDR3 sequences which differ from those of the anti-OX40 antibodies of the present invention by one or more conservative modifications. It is understood in the art that certain conservative sequence modification can be made which do not remove antigen binding. See, e.g., Brummell et al., (1993) Biochem 32:1180-8; de Wildt et al., (1997) Prot. Eng. 10:835-41; Komissarov et al., (1997) J Biol. Chem. 272:26864-26870; Hall et al., (1992) J. Immunol. 149:1605-12; Kelley and O'Connell (1993) Biochem. 32:6862-35; Adib-Conquy et al., (1998) Int. Immunol. 10:341-6 and Beers et al., (2000) Clin. Can. Res. 6:2835-43.

Accordingly, in one embodiment, the antibody comprises a heavy chain variable region comprising CDR1, CDR2, and CDR3 sequences and/or a light chain variable region comprising CDR1, CDR2, and CDR3 sequences, wherein:
(a) the heavy chain variable region CDR1 sequence comprises a sequence listed in Table 1 above, and/or conservative modifications thereof; and/or
(b) the heavy chain variable region CDR2 sequence comprises a sequence listed in Table 1 above, and/or conservative modifications thereof; and/or
(c) the heavy chain variable region CDR3 sequence comprises a sequence listed in Table 1 above, and conservative modifications thereof; and/or
(d) the light chain variable region CDR1, and/or CDR2, and/or CDR3 sequences comprise the sequence(s) listed in Table 1 above; and/or conservative modifications thereof; and
(e) the antibody specifically binds human OX40.

The antibody of the present invention possesses one or more of the following functional properties described above, such as high affinity binding to human OX40, and the ability to induce ADCC or CDC against OX40-expressing cells.

In various embodiments, the antibody can be, for example, a mouse, human, humanized or chimeric antibody.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for retained function (i.e., the functions set forth above) using the functional assays described herein.

Engineered and Modified Antibodies

Antibodies of the invention can be prepared using an antibody having one or more of the $V_H/V_L$ sequences of the anti-OX40 antibody of the present invention as starting material to engineer a modified antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

In certain embodiments, CDR grafting can be used to engineer variable regions of antibodies. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann et al., (1998) Nature 332:323-327; Jones et al., (1986) Nature 321:522-525; Queen et al., (1989) Proc. Natl. Acad. See also U.S.A. 86:10029-10033; U.S. Pat. Nos. 5,225,539; 5,530,101; 5,585,089; 5,693,762 and 6,180,370).

Accordingly, another embodiment of the invention pertains to an isolated monoclonal antibody, or antigen binding portion thereof, comprising a heavy chain variable region comprising CDR1, CDR2, and CDR3 sequences comprising the sequences of the present invention, as described above, and/or a light chain variable region comprising CDR1, CDR2, and CDR3 sequences comprising the sequences of the present invention, as described above. While these antibodies contain the $V_H$ and $V_L$ CDR sequences of the monoclonal antibody of the present invention, they can contain different framework sequences.

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat et al., (1991), cited supra; Tomlinson et al., (1992) J. Mol. Biol. 227:776-798; and Cox et al., (1994) Eur. J. Immunol. 24:827-836; the contents of each of which are expressly incorporated herein by reference. As another example, the germline DNA sequences for human heavy and light chain variable region genes can be found in the Genbank database. For example, the following heavy chain germline sequences found in the HCo7 HuMAb mouse are available in the accompanying Genbank Accession Nos.: 1-69 (NG--0010109, NT--024637 & BC070333), 3-33 (NG--0010109 & NT--024637) and 3-7

(NG--0010109 & NT--024637). As another example, the following heavy chain germline sequences found in the HCo12 HuMAb mouse are available in the accompanying Genbank Accession Nos.: 1-69 (NG--0010109, NT--024637 & BC070333), 5-51 (NG--0010109 & NT--024637), 4-34 (NG--0010109 & NT--024637), 3-30.3 (CAJ556644) & 3-23 (AJ406678).

Antibody protein sequences are compared against a compiled protein sequence database using one of the sequence similarity searching methods called the Gapped BLAST (Altschul et al., (1997), supra), which is well known to those skilled in the art.

Preferred framework sequences for use in the antibodies of the invention are those that are structurally similar to the framework sequences used by antibodies of the invention. The $V_H$ CDR1, CDR2, and CDR3 sequences can be grafted onto framework regions that have the identical sequence as that found in the germline immunoglobulin gene from which the framework sequence derives, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370).

Another type of variable region modification is to mutate amino acid residues within the $V_H$ and/or $V_L$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as known in the art. Preferably conservative modifications (as known in the art) are introduced. The mutations can be amino acid substitutions, additions or deletions, but are preferably substitutions. Moreover, typically no more than one, two, three, four or five residues within a CDR region are altered.

Accordingly, in another embodiment, the invention provides isolated anti-OX40 monoclonal antibodies, or antigen binding portions thereof, comprising a heavy chain variable region comprising: (a) a $V_H$ CDR1 region comprising the sequence of the present invention, or an amino acid sequence having one, two, three, four or five amino acid substitutions, deletions or additions; (b) a $V_H$ CDR2 region comprising the sequence of the present invention, or an amino acid sequence having one, two, three, four or five amino acid substitutions, deletions or additions; (c) a $V_H$ CDR3 region comprising the sequence of the present invention, or an amino acid sequence having one, two, three, four or five amino acid substitutions, deletions or additions; (d) a $V_L$ CDR1 region comprising the sequence of the present invention, or an amino acid sequence having one, two, three, four or five amino acid substitutions, deletions or additions; (e) a $V_L$ CDR2 region comprising the sequence of the present invention, or an amino acid sequence having one, two, three, four or five amino acid substitutions, deletions or additions; and (f) a $V_L$ CDR3 region comprising the sequence of the present invention, or an amino acid sequence having one, two, three, four or five amino acid substitutions, deletions or additions.

Engineered antibodies of the invention include those in which modifications have been made to framework residues within $V_H$ and/or $V_L$, e.g. to improve the properties of the antibody. Typically, such framework modifications are made to decrease the immunogenicity of the antibody. For example, one approach is to "backmutate" one or more framework residues to the corresponding germline sequence. More specifically, an antibody that has undergone somatic mutation can contain framework residues that differ from the germline sequence from which the antibody is derived. Such residues can be identified by comparing the antibody framework sequences to the germline sequences from which the antibody is derived.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043.

In addition, or as an alternative to modifications made within the framework or CDR regions, antibodies of the invention can be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention can be chemically modified (e.g., one or more chemical moieties can be attached to the antibody) or be modified to alter its glycosylation, again to alter one or more functional properties of the antibody.

In one embodiment, the hinge region of $C_{H1}$ is modified in such that the number of cysteine residues in the hinge region is altered, e.g., increased or decreased. This approach is described further in U.S. Pat. No. 5,677,425. The number of cysteine residues in the hinge region of Cm is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the $C_{H2}$-$C_{H3}$ domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745.

In still another embodiment, the glycosylation of an antibody is modified. For example, a glycosylated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. See, e.g., U.S. Pat. Nos. 5,714,350 and 6,350,861.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, the cell lines Ms704, Ms705, and Ms709 lack the fucosyltransferase gene, FUT8 (α(1,6)-fucosyltransferase), such that antibodies expressed in the Ms704, Ms705, and Ms709 cell lines lack fucose on their carbohydrates. The Ms704, Ms705, and Ms709 FUT8−/− cell lines were created by the targeted disruption of the FUT8 gene in CHO/DG44 cells using two replacement vectors (see U.S. Patent Publication No. 20040110704 and Yamane-Ohnuki et al., (2004) Biotechnol Bioeng 87:614-22). As another example, EP 1,176,195 describes a cell line with a functionally disrupted FUT8 gene, which encodes a fucosyl transferase, such that antibodies expressed in such a cell line exhibit hypofucosylation by reducing or eliminating the α-1,6 bond-related enzyme. EP 1,176,195 also describes cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 describes a variant CHO cell line, Lec13 cells, with reduced ability to attach fucose to Asn(297)-linked carbohydrates, also resulting in hypofucosylation of antibodies expressed in that host cell (see also Shields et al., (2002) J. Biol. Chem. 277: 26733-26740). Antibodies with a modified glycosylation profile can also be produced in chicken eggs, as described in PCT Publication WO 06/089231. Alternatively, antibodies with a modified glycosylation profile can be produced in plant cells, such as Lemna. Methods for production of antibodies in a plant system are disclosed in the U.S. patent application corresponding to Alston & Bird LLP Ser. No. 60/836,998, filed on Aug. 11, 2006. PCT Publication WO 99/54342 describes cell lines engineered to express glycoprotein-modifying glycosyltransferases (e.g., β(1,4)-N-acetylglucosaminyltransferase III (GnTIII)) such that antibodies expressed in the engineered cell lines exhibit increased bisecting GlcNac structures which results in increased ADCC activity of the antibodies (see also Umana et al., (1999) Nat. Biotech. 17:176-180). Alternatively, the fucose residues of the antibody can be cleaved off using a fucosidase enzyme; e.g., the fucosidase α-L-fucosidase removes fucosyl residues from antibodies (Tarentino et al., (1975) Biochem. 14:5516-23).

Another modification of the antibodies herein that is contemplated by this disclosure is pegylation. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono ($C_1$-$C_{10}$) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See, e.g., EPO 154 316 and EP 0 401 384.

Antibody's Physical Properties

Antibodies of the invention can be characterized by their various physical properties, to detect and/or differentiate different classes thereof.

For example, antibodies can contain one or more glycosylation sites in either the light or heavy chain variable region. Such glycosylation sites may result in increased immunogenicity of the antibody or an alteration of the pK of the antibody due to altered antigen binding (Marshall et al (1972) Annu Rev Biochem 41:673-702; Gala and Morrison (2004) J Immunol 172:5489-94; Wallick et al (1988) J Exp Med 168:1099-109; Spiro (2002) Glycobiology 12:43R-56R; Parekh et al (1985) Nature 316:452-7; Mimura et al., (2000) Mol Immunol 37:697-706). Glycosylation has been known to occur at motifs containing an N-X-S/T sequence. In some instances, it is preferred to have an anti-OX40 antibody that does not contain variable region glycosylation. This can be achieved either by selecting antibodies that do not contain the glycosylation motif in the variable region or by mutating residues within the glycosylation region.

In a preferred embodiment, the antibodies do not contain asparagine isomerism sites. The deamidation of asparagine may occur on N-G or D-G sequences and result in the creation of an isoaspartic acid residue that introduces a kink into the polypeptide chain and decreases its stability (isoaspartic acid effect).

Each antibody will have a unique isoelectric point (pI), which generally falls in the pH range between 6 and 9.5. The pI for an IgG1 antibody typically falls within the pH range of 7-9.5 and the pI for an IgG4 antibody typically falls within the pH range of 6-8. There is speculation that antibodies with a pI outside the normal range may have some unfolding and instability under in vivo conditions. Thus, it is preferred to have an anti-OX40 antibody that contains a pI value that falls in the normal range. This can be achieved either by selecting antibodies with a pI in the normal range or by mutating charged surface residues.

Nucleic Acid Molecules Encoding Antibodies of the Invention

In another aspect, the invention provides nucleic acid molecules that encode heavy and/or light chain variable regions, or CDRs, of the antibodies of the invention. The nucleic acids can be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques. A nucleic acid of the invention can be, e.g., DNA or RNA and may or may not contain intronic sequences. In a preferred embodiment, the nucleic acid is a cDNA molecule.

Nucleic acids of the invention can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), a nucleic acid encoding such antibodies can be recovered from the gene library.

Preferred nucleic acids molecules of the invention include those encoding the $V_H$ and $V_L$ sequences of the OX40 monoclonal antibody or the CDRs. Once DNA fragments encoding $V_H$ and $V_L$ segments are obtained, these DNA fragments can be further manipulated by standard recombinant DNA techniques, for example to convert the variable region genes to full-length antibody chain genes, to Fab fragment genes or to a scFv gene. In these manipulations, a $V_L$- or $V_H$-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the $V_H$-encoding DNA to another DNA molecule encoding heavy chain constant regions ($C_{H1}$, $C_{H2}$ and $C_{H3}$). The sequences of human heavy chain constant region genes are known in the art and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the $V_H$-encoding DNA can be operatively linked to another DNA molecule encoding only the heavy chain $C_{H1}$ constant region.

The isolated DNA encoding the $V_L$ region can be converted to a full-length light chain gene (as well as a Fab light chain gene) by operatively linking the $V_L$-encoding DNA to another DNA molecule encoding the light chain constant region, $C_L$. The sequences of human light chain constant region genes are known in the art and DNA fragments encompassing these regions can be obtained by standard PCR amplification. In preferred embodiments, the light chain constant region can be a kappa or lambda constant region.

To create a scFv gene, the $V_H$- and $V_L$-encoding DNA fragments are operatively linked to another fragment encoding a flexible linker, e.g., encoding the amino acid sequence (Gly4-Ser)3, such that the $V_H$ and $V_L$ sequences can be expressed as a contiguous single-chain protein, with the $V_L$ and $V_H$ regions joined by the flexible linker (see e.g., Bird et al., (1988) *Science* 242:423-426; Huston et al., (1988) *Proc. Natl. Acad. Sci. USA* 85:5879-5883; McCafferty et al., (1990) *Nature* 348:552-554).

Production of Monoclonal Antibodies of the Invention

Monoclonal antibodies (mAbs) of the present invention can be produced using the well-known somatic cell hybridization (hybridoma) technique of Kohler and Milstein (1975) *Nature* 256: 495. Other embodiments for producing monoclonal antibodies include viral or oncogenic transformation of B lymphocytes and phage display techniques. Chimeric or humanized antibodies are also well known in the art. See e.g., U.S. Pat. Nos. 4,816,567; 5,225,539; 5,530,101; 5,585,089; 5,693,762 and 6,180,370, the contents of which are specifically incorporated herein by reference in their entirety.

Generation of Transfectomas Producing Monoclonal Antibodies of the Invention

Antibodies of the invention also can be produced in a host cell transfectoma using, for example, a combination of recombinant DNA techniques and gene transfection methods as is well known in the art (e.g., Morrison, S. (1985) *Science* 229:1202). In one embodiment, DNA encoding partial or full-length light and heavy chains obtained by standard molecular biology techniques is inserted into one or more expression vectors such that the genes are operatively linked to transcriptional and translational regulatory sequences. In this context, the term "operatively linked" is intended to mean that an antibody gene is ligated into a vector such that transcriptional and translational control sequences within the vector serve their intended function of regulating the transcription and translation of the antibody gene.

The term "regulatory sequence" is intended to include promoters, enhancers and other expression control elements (e.g., polyadenylation signals) that control the transcription or translation of the antibody genes. Such regulatory sequences are described, e.g., in Goeddel (Gene Expression Technology. Methods in Enzymology 185, Academic Press, San Diego, Calif. (1990)). Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, e.g., the adenovirus major late promoter (AdMLP) and polyoma. Alternatively, nonviral regulatory sequences can be used, such as the ubiquitin promoter or β-globin promoter. Still further, regulatory elements composed of sequences from different sources, such as the SRα promoter system, which contains sequences from the SV40 early promoter and the long terminal repeat of human T cell leukemia virus type 1 (Takebe et al., (1988) Mol. Cell. Biol. 8:466-472). The expression vector and expression control sequences are chosen to be compatible with the expression host cell used.

The antibody light chain gene and the antibody heavy chain gene can be inserted into the same or separate expression vectors. In preferred embodiments, the variable regions are used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_L$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes and regulatory sequences, the recombinant expression vectors of the invention can carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216; 4,634,665 and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody.

Preferred mammalian host cells for expressing the recombinant antibodies of the invention include Chinese Hamster Ovary (CHO cells) (including dhfr– CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *J. Mol. Biol.* 159:601-621), NS0 myeloma cells, COS cells and SP2 cells. In particular for use with NS0 myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Immunoconjugates

Antibodies of the invention can be conjugated to a therapeutic agent to form an immunoconjugate such as an antibody-drug conjugate (ADC). Suitable therapeutic agents include cytotoxins, alkylating agents, DNA minor groove binders, DNA intercalators, DNA crosslinkers, histone deacetylase inhibitors, nuclear export inhibitors, proteasome inhibitors, topoisomerase I or II inhibitors, heat shock protein inhibitors, tyrosine kinase inhibitors, antibiotics, and anti-mitotic agents. In the ADC, the antibody and therapeutic agent preferably are conjugated via a linker cleavable such as a peptidyl, disulfide, or hydrazone linker. More preferably, the linker is a peptidyl linker such as Val-Cit, Ala-Val, Val-Ala-Val, Lys-Lys, Pro-Val-Gly-Val-Val, Ala-Asn-Val, Val-Leu-Lys, Ala-Ala-Asn, Cit-Cit, Val-Lys, Lys, Cit, Ser, or Glu. The ADCs can be prepared as described in U.S. Pat. Nos. 7,087,600; 6,989,452; and 7,129,261; PCT Publications WO 02/096910; WO 07/038,658; WO 07/051,081; WO 07/059,404; WO 08/083,312; and WO 08/103,693; U.S. Patent Publications 20060024317; 20060004081; and 20060247295; the disclosures of which are incorporated herein by reference.

Bispecific Molecules

In another aspect, the present disclosure features bispecific molecules comprising one or more antibodies of the invention linked to at least one other functional molecule, e.g., another peptide or protein (e.g., another antibody or ligand for a receptor) to generate a bispecific molecule that binds to at least two different binding sites or target molecules. Thus, as used herein, "bispecific molecule" includes molecules that have three or more specificities.

In an embodiment, a bispecific molecule has, in addition to an anti-Fc binding specificity and an anti-OX40 binding specificity, a third specificity. The third specificity can be for an anti-enhancement factor (EF), e.g., a molecule that binds to a surface protein involved in cytotoxic activity and thereby increases the immune response against the target cell. For example, the anti-enhancement factor can bind a cytotoxic T-cell (e.g. via CD2, CD3, CD8, CD28, CD4, CD40, or ICAM-1) or other immune cell, resulting in an increased immune response against the target cell.

Bispecific molecules may be in many different formats and sizes. At one end of the size spectrum, a bispecific molecule retains the traditional antibody format, except that, instead of having two binding arms of identical specificity, it has two binding arms each having a different specificity. At the other extreme are bispecific molecules consisting of two single-chain antibody fragments (scFv's) linked by a peptide chain, a so-called Bs(scFv)2 construct. Intermediate-sized bispecific molecules include two different F(ab) fragments linked by a peptidyl linker. Bispecific molecules of these and other formats can be prepared by genetic engineering, somatic hybridization, or chemical methods. See, e.g., Kufer et al, cited supra; Cao and Suresh, *Bioconjugate Chemistry*, 9 (6), 635-644 (1998); and van Spriel et al., *Immunology Today*, 21 (8), 391-397 (2000), and the references cited therein.

Antibody-Encoding or Antibody-Bearing Oncolytic Virus

An oncolytic virus preferabtially infects and kills cancer cells. Antibodies of the present invention can be used in conjunction with oncolytic viruses. Alternatively, oncolytic viruses encoding antibodies of the present invention can be introduced into human body.

Pharmaceutical Compositions

In another aspect, the present disclosure provides a pharmaceutical composition comprising one or more antibodies of the present invention formulated together with a pharmaceutically acceptable carrier. The composition may optionally contain one or more additional pharmaceutically active ingredients, such as another antibody or a drug. The pharmaceutical compositions of the invention also can be administered in a combination therapy with, for example, another anti-cancer agent, another anti-inflammatory agent, or an antimicrobial agent.

The pharmaceutical composition can comprise any number of excipients. Excipients that can be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients is taught in Gennaro, ed., Remington: *The Science and Practice of Pharmacy*, 20th Ed. (Lippincott Williams & Wilkins 2003), the disclosure of which is incorporated herein by reference.

Preferably, the pharmaceutical composition is suitable for intravenous, intramuscular, subcutaneous, parenteral, spinal or epidermal administration (e.g., by injection or infusion). Depending on the route of administration, the active ingredient can be coated in a material to protect it from the action of acids and other natural conditions that may inactivate it. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, an antibody of the invention can be administered via a non-parenteral route, such as a topical, epidermal or mucosal route of administration, e.g., intranasally, orally, vaginally, rectally, sublingually or topically.

Pharmaceutical compositions can be in the form of sterile aqueous solutions or dispersions. They can also be formulated in a microemulsion, liposome, or other ordered structure suitable to high drug concentration.

The amount of active ingredient which can be combined with a carrier material to produce a single dosage form will vary depending upon the subject being treated and the particular mode of administration and will generally be that amount of the composition which produces a therapeutic effect. Generally, out of one hundred percent, this amount will range from about 0.01% to about ninety-nine percent of active ingredient, preferably from about 0.1% to about 70%, most preferably from about 1% to about 30% of active ingredient in combination with a pharmaceutically acceptable carrier.

Dosage regimens are adjusted to provide the optimum desired response (e.g., a therapeutic response). For example, a single bolus can be administered, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active ingredient calculated to produce the desired therapeutic effect in association with the required pharmaceutical carrier. Alternatively, antibody can be administered as a sustained release formulation, in which case less frequent administration is required.

For administration of the antibody, the dosage may range from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for an anti-OX40 antibody of the invention include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks. In some methods, dosage is adjusted to achieve a plasma antibody concentration of about 1-1000 µg/ml and in some methods about 25-300 µg/ml.

A "therapeutically effective dosage" of an anti-OX40 antibody of the invention preferably results in a decrease in severity of disease symptoms, an increase in frequency and duration of disease symptom-free periods, or a prevention of impairment or disability due to the disease affliction. For example, for the treatment of tumor-bearing subjects, a "therapeutically effective dosage" preferably inhibits tumor growth by at least about 20%, more preferably by at least about 40%, even more preferably by at least about 60%, and still more preferably by at least about 80% relative to untreated subjects. A therapeutically effective amount of a therapeutic antibody can decrease tumor size, or otherwise ameliorate symptoms in a subject, which is typically a human or can be another mammal.

The pharmaceutical composition can be a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. See, e.g., Sustained and Controlled Release Drug Delivery Systems, J. R. Robinson, ed., Marcel Dekker, Inc., New York, 1978.

Therapeutic compositions can be administered via medical devices such as (1) needleless hypodermic injection devices (e.g., U.S. Pat. Nos. 5,399,163; 5,383,851; 5,312, 335; 5,064,413; 4,941,880; 4,790,824; and 4,596,556); (2) micro-infusion pumps (U.S. Pat. No. 4,487,603); (3) transdermal devices (U.S. Pat. No. 4,486,194); (4) infusion apparatuses (U.S. Pat. Nos. 4,447,233 and 4,447,224); and (5) osmotic devices (U.S. Pat. Nos. 4,439,196 and 4,475, 196); the disclosures of which are incorporated herein by reference.

In certain embodiments, the monoclonal antibodies of the invention can be formulated to ensure proper distribution in vivo. For example, to ensure that the therapeutic antibody of the invention cross the blood-brain barrier, they can be formulated in liposomes, which may additionally comprise targeting moieties to enhance selective transport to specific cells or organs. See, e.g. U.S. Pat. Nos. 4,522,811; 5,374, 548; 5,416,016; and 5,399,331; V. V. Ranade (1989) *J. Clin. Pharmacol.* 29:685; Umezawa et al., (1988) *Biochem. Biophys. Res. Commun.* 153:1038; Bloeman et al., (1995) *FEBS Lett.* 357:140; M. Owais et al., (1995) *Antimicrob. Agents Chemother.* 39:180; Briscoe et al., (1995) *Am. J. Physiol.* 1233:134; Schreier et al., (1994) *J. Biol. Chem.* 269:9090; Keinanen and Laukkanen (1994) *FEBS Lett.* 346:123; and Killion and Fidler (1994) *Immunomethods* 4:273.

Uses and Methods of the Invention

Antibodies (compositions, bispecifics, and immunoconjugates) of the present invention have numerous in vitro and in vivo utilities involving, for example, treatment and/or prevention of cancers. The antibodies can be administered to human subjects, e.g., in vivo, to inhibit tumor growth.

Given the ability of anti-OX40 antibodies of the invention to inhibit proliferation and survival of cancer cells, the invention provides methods for inhibiting growth of tumor cells in a subject comprising administering to the subject an antibody of the invention such that growth of the tumor is inhibited in the subject. Non-limiting examples of tumors that can be treated by antibodies of the invention include, but not limited to, lymphoma, melanoma, sarcoma, colon cancer, breast cancer, glioma, head and neck squamous cell carcinoma, non-small cell lung cancer, and colon adenocarcinoma, original and/or metastatic. Additionally, refractory or recurrent malignancies whose growth may be inhibited using the antibodies of the invention.

In another aspect, the invention provides a method for treating an infectious disease in a subject, comprising administering to the subject a therapeutically effective amount of the antibody, or antigen-binding portion thereof, of the invention. Additional anti-infective agents can be administered with the antibody, or an antigen-binding portion thereof, of the invention, such as antibacterial, antiviral, antifungal, and antiparasitic agents.

Generally speaking, the antibodies of the invention can be used to enhance an immune response in a subject.

These and other methods of the invention are discussed in further detail below.

Combination Therapy

In another aspect, the invention provides methods of combination therapy in which an anti-OX40 antibody (or antigen-binding portion thereof) of the present invention is co-administered with one or more additional antibodies that are effective in inhibiting tumor growth in a subject. In one embodiment, the invention provides a method for inhibiting tumor growth in a subject comprising administering to the subject an anti-OX40 antibody and one or more additional antibodies, such as an anti-LAG-3 antibody, an anti-PD-L1 antibody, and anti-PD-1 antibody and/or an anti-CTLA-4 antibody. In certain embodiments, the subject is human.

The present invention also provides a method for inhibiting tumor growth in a subject comprising administering to the subject an anti-OX40 antibody and an agent activating OX40 expression. Expression of OX40 is preferably on the cell surface of a T cell. The agent can be a TLR9 ligand, or specifically an unmethylated CpG oligonucleotide. Alternatively, the agent can be phytohemagglutinin-leucoagglutinin, or IL-2.

The OX40 signaling activation can also be further combined with standard cancer treatments. For example, OX40 signaling activationa can be combined with CTLA-4 and/or LAG-3 and/or PD-1 blockade and also chemotherapeutic regimes. For example, a chemotherapeutic agent can be administered with the anti-OX40 antibodies, which may be a cytotoxic agent. For example, epitubicin, oxaliplatin, and 5-FU are administered to patients receiving anti-OX40 therapy.

Optionally, the combination of anti-OX40 and one or more additional antibodies (e.g., anti-CTLA-4 and/or anti-LAG-3 and/or anti-PD-1 antibodies) can be further combined with an immunogenic agent, such as cancerous cells, purified tumor antigens (including recombinant proteins, peptides, and carbohydrate molecules), and cells transfected with genes encoding immune stimulating cytokines (He et al., (2004) J. Immunol. 173:4919-28). Non-limiting examples of tumor vaccines that can be used include peptides of melanoma antigens, such as peptides of gp100, MAGE antigens, Trp-2, MARTI_ and/or tyrosinase, or tumor cells transfected to express the cytokine GM-CSF.

Other therapies that may be combined with anti-OX40 antibody includes, but not limited to, interleukin-2 (IL-2) administration, radiation, surgery, or hormone deprivation.

The combination of therapeutic agents discussed herein can be administered concurrently as a single composition in a pharmaceutically acceptable carrier, or concurrently as separate compositions with each agent in a pharmaceutically acceptable carrier. In another embodiment, the combination of therapeutic agents can be administered sequentially.

Furthermore, if more than one dose of the combination therapy is administered sequentially, the order of the sequential administration can be reversed or kept in the same order at each time point of administration, sequential administrations can be combined with concurrent administrations, or any combination thereof.

The present disclosure is further illustrated by the following examples, which should not be construed as further limiting. The contents of all figures and all references, Genbank sequences, patents and published patent applications cited throughout this application are expressly incorporated herein by reference.

Examples

Example 1 Construction of HEK293A Cell Lines Stably Expressing Human, Rhesus or Mouse OX40

Stable cell lines overexpressing human, rhesus or mouse OX40 were constructed using HEK293A cells (Cobioer, N.J., China). Briefly, human, rhesus or mouse OX40 cDNA sequence (SEQ ID NOs: 31, 33 and 35, encoding amino acid sequences set forth in SEQ ID NOs: 32, 34 and 36, respectively) were synthesized, and then subcloned into pLV-EGFP(2A)-Puro vectors. Lenti viruses were generated in HEK-293T cells (Cobioer, N.J., China) by cotransfection of pLV-EGFP(2A)-Puro-OX40, psPAX and pMD2.G plasmids, according to the instruction in Lipofectamine 3000 kit (Thermo Fisher Scientific, US). Three days post cotransfection, the lenti viruses were harvested from the cell culture medium (DMEM medium (Cat #: SH30022.01, Gibco) with 10% FBS (Cat #: FND500, Excell)) of respective HEK-293T cells. Finally, HEK293A cells were infected with the lenti viruses to generate HEK293A cell lines stably expressing human, rhesus or mouse OX40, namely HEK293A/huOX40, HEK293A/rhOX40 or HEK293A/muOX40 cells. Transfected HEK293A cells were then cultured in medium (DMEM+10% FBS) containing 0.2 µg/ml puromycin (Cat #: A11138-03, Gibco) for 7 days. The expression of human OX40 and rhesus OX40 were confirmed by FACS using a commercially available anti-human OX40 antibody (PE-anti-human OX40, Biolegend, US, Cat #: 350003, Lot no.: B228541). Similarly, the expression of mouse OX40 was confirmed by FACS using an anti-mouse OX40 antibody (PE-anti-mouse OX40, Biolegend, US, Cat#: 119409, Lot no.: B229283).

Example 2 Generation of Hybridoma Cell Lines Producing Monoclonal Antibodies Against Human OX40

Murine anti-human OX40 monoclonal antibodies (mAbs) were generated using the conventional hybridoma fusion technology with some modifications.

Inoculation

Twenty BALB/c mice (Beijing Vital River Laboratory Animal Technology Co., Ltd, Beijing, China) were inoculated with recombinant human OX40(ECD)-hFc (Sino Biological, CN, Cat#: 10481-H08H, Lot no.: LC11AP2001) and/or recombinant rhesus OX40-his (Sino Biological, CN, Cat#:90846-C08H, Lot no.:MB110C1803) following the scheme in Table 2 below. The human OX40 (ECD)-hFc and rhesus OX40-his were emulsified by sonication with an equal volume of Complete Freund's Adjuvant (SIGMA, USA, Cat#: F5881-10*10ML, Lot no.: SLBV0593), Incomplete Freund's Adjuvant (SIGMA, USA, Cat#: F5506-6*10ML, Lot no.: SLBR3892V), or PBS.

TABLE 2

| | Inoculation scheme | | | | |
| --- | --- | --- | --- | --- | --- |
| | Primary | 1st Boost | 2nd Boost | 3rd Boost | Final Boost |
| Date of inoculation | 2017 Dec. 04 | 2017 Dec. 18 | 2018 Jan. 01 | 2018 Jan. 15 | 2018 Jan. 22 |
| Protein and dose for inoculation | Human OX40(ECD)-hfc (50 µg/mouse) | Human OX40(ECD)-hFc (50 µg/mouse) | Human OX40(ECD)-hFc (25 µg/mouse) + Rhesus OX40-his (25 µg/mouse) | Human OX40(ECD)-hFc (25 µg/mouse) + Rhesus OX40-his (25 µg/mouse) | Human OX40(ECD)-hFc (50 µg/mouse) |
| Adjuvant | Complete Freund's | Incomplete Freund's | Incomplete Freund's | Incomplete Freund's | PBS |
| Way of inoculation | i.p. | s.c. | i.p. | s.c. | i.p. |

One week after each boost, 50 µl of murine serum was collected from each mouse for titer determination by ELISA using the recombinant human OX40-his (Sino Biological, CN, Cat#:10481-H03H) and Rhesus OX40-his (Sino Biological, CN, Cat#: 90846-C08H). Titer determination was also done by FACS using HEK293A overexpressing human OX40, rhesus OX40 and mouse OX40 as prepared in Example 1.

Based on the ELISA and FACS analysis results after the final boost, seven mice which showed high serum titers were chosen for hybridoma cell line generation.

Generation of Hybridoma Cell Lines

Hybridoma cell lines were generated using the conventional hybridoma fusion technology with minor modifications.

Prior to cell fusion, each selected mouse was boosted intraperitoneally with human OX40(ECD)-hFc in PBS once, at a dose of 50 µg per mouse. Four days latter, mice were sacrificed, and spleens were collected and prepared as single cell suspensions in PBS. The spleenocytes were washed for three times with DMEM medium (Hyclone, Cat#: SH30243.01B). Viable myeloma cells SP2/0 (ATCC, CRL-1581) at the log-phase were mixed with the murine spleenocytes in a ratio of 1:4. The cells were then washed 2 times and then cell fusion was performed with PEG (Sigma, Cat#: P7181). The post-fusion cells were washed with DMEM medium for three times and suspended in cell growth media (RPMI medium 1640 (Gibco, Cat. C22400500CP)) supplemented with 10% FBS and 1×HAT (Sigma, H0262). The cell suspension was plated into 96 well cell culture plates, 200 µl per well ($5 \times 10^4$ cells/well), and incubated in a 37° C. humidified 10% $CO_2$ incubator for 7 days. At day 7, the growth media was replaced by fresh growth media supplemented with 10% FBS+1×HT (Sigma, H0137). 2-3 days later, hybridoma cells were screened by ELISA and FACS.

Screening of Hybridoma Cell Lines by ELISA

High-throughput ELISA binding assay was firstly used to screen for hybridoma clones binding to human OX40. Hybridoma clones binding to human OX40 were further tested for their ability to cross-react with rhesus or mouse OX40.

For ELISA assays, 96-well ELISA plates were coated with 100 µl/well human OX40-His (0.5 µg/ml, Sino Biological, CN, Cat#:10481-H03H), rhesus OX40-His (0.5 µg/ml, Sino Biological, CN, Cat#: 90846-C08H) or murine OX40-His (0.5 µg/ml, Crown, CN, Cat#: E3350-B1707) at room temperature overnight. Plates were washed 3 times with PBST buffer (PBS+0.05% Tween 20) and blocked with 200 µl of blocking buffer (PBS containing 1% BSA, 1% goat serum, and 0.05% Tween 20) at RT for 2 hr and washed for 3 times with PBST. Then, hybridoma cell culture supernatant was diluted 10× with dilution buffer (PBS containing 1% BSA, 1% goat serum, 0.01% Tween 20) and added to the plates, 100 µl per well. After incubated at RT for 1 hr, plates were washed 3 times with PBST and then 100 µl of goat anti-mouse Fc-HRP (1:5000, Sigma, US, Cat#:A9309-1 ml) was added to each well. After incubated at RT for 1 hr, plates were washed 3 times with PBST and then 80 µl of TMB was added to each well. Five to ten minutes later, 80 µl of 0.16 M sulfuric acid was added to each well and then OD450 was read on SpectraMaxR i3× (Molecular Devies, US).

With the ELISA assays, 209 hybridoma clones were identified to have specific binding to both human and rhesus monkey OX40.

Screening of Hybridoma Cell Lines by FACS

The 209 Hybridoma clones were further screened for their binding capacity to human, rhesus or mouse OX40 expressed on HEK293A cells. Briefly, 100,000 HEK293A/human OX40 cells, HEK293A/rhesusOX40 cells or HEK293A/mouseOX40 cells as prepared in Example 1 were seeded into each well of the 96-well plates and hybridoma cell culture supernatant diluted 10 times with dilution buffer (PBS plus 1% BSA, 1% goat serum, 0.01% Tween 20) was added to the plates (100 µl/well). After incubated at 4° C. for 1 hour, plates were washed 3 times with FACS solution (PBS+1% BSA+0.01% Tween 20). Then, cells were suspended in FACS solution, and APC goat anti-mouse IgG (BioLegen, US, Cat#: 405308) diluted 500× was added to the plates. After incubation at 4° C. for 1 hour, plates were washed with PBS for 3 times and then the cell fluorescence was monitored using a FACS machine (BD).

Based on the FACS screening, 177 positive clones were obtained that displayed high binding capacity to both HEK293A/humanOX40 and HEK293A/rhesusOX40 cells and did not bind to HEK293A/mouseOX40 cells.

Subcloning of Hybridoma Clones Producing Anti-OX40 Antibodies

The 177 hybridoma clones were subject to 2 rounds of subcloning. During the subcloning, multiple subclones (n>3) from each parent clone were selected and confirmed by ELISA and FACS assays as described above. The subclones selected through this process were defined as hybridoma cells producing monoclonal antibodies. Finally, 84 subclones (one subclone from each parent clone) having high binding capacity to both human and monkey OX40 were obtained.

Screening of Hybridoma Cell Lines by HEK Blue Activity Assay

The 84 subclones were expanded in 96-well plates and then cultured for 5 days. Supernatants were harvested for HEK-Blue activity assays to identify OX40 antibodies having agonist activity to human OX40.

Briefly, a stable HEK-Blue reporter cell line expressing human OX40-CD40 fusion protein (SEQ ID NO.: 37) (referred to as HEK-Blue/OX40) was established by infecting HEK-Blue null 1_v cells (InvivoGen, San Diego, Calif.) with OX40-CD40 fusion protein-expressing lentivirus (which was generated as described above in Example 1), followed by selection with 10 µg/ml puromycin.

For HEK-Blue reporter assay, 40000 HEK-Blue/OX40 cells suspended in 200 µl of culture media (DMEM medium (Hyclone, USA, Cat#: SH30243.01)+10% FBS (Excell, China, Cat#: FND500)+10 µg/ml Puromycin (GIBCO, USA, Cat#: A11138-03)+100 µg/ml Normocin™ (Invivogen, USA, Cat#: ant-nr-2)+100 µg/ml Zeocin (Invivogen, USA, Cat#: ant-Zn-5)) were plated in a 96-well plate and cultured at 37° C. overnight. On the 2nd day, 200 µl of DMEM medium was added to each well to replace the culture medium. Seven hours later, the DMEM medium in the well was replaced with 200 µL/well HEK Blue Detection buffer (Invivogen; US; Cat#: hb-det3; Lot no.: HKB-3903). One millimeter of hybridoma cell culture supurnatant was incubated with 20 µl of protein G agarose ((Santa Cruz Biotechnology; US; Cat#: SC-2002) for 30 mins at RT to enrich the antibodies, and then the enriched antibodies were added to the above HEK-Blue/OX40 cells. The resultant mixtures were incubated at 37° C. under 5% $CO_2$ until the appropriate blue color developed. OD650 was measured using a SpectraMax microplate reader (Molecular Devices; US; SpectraMaxR i3X). Fresh hybridoma culture medium was used as negative control and OX40L (Sino biological, China, Cat#:13127-H01H), the natural ligand and activator of OX40, was used as positive control.

As shown in FIG. 1, 47 clones displayed different levels of OX40 agonist activity.

Example 3 Purification of Anti-OX40 Monoclonal Antibodies

Based on the HEK-Blue assays as mentioned above, 33 clones (see Table 3 below) with high HEK-Blue activity were selected for further characterizations. Monoclonal antibodies from the 33 selected clones were purified. Briefly, hybridoma cells of each subclone were grown in T175 cell culture flasks each having 100 ml of fresh serum-free medium (Gibco, US, Cat#: 12045-076) with 1% HT supplement (Gibco, Cat#: 11067-030). Cell cultures were kept for 10 days in an incubator with 5% $CO_2$ at 37° C. Cell cultures were collected, followed by centrifugation at 3500 rpm for 5 minutes and then subject to filtration using a 0.22 µm capsule to remove the cell debris. Monoclonal antibodies were then purified using a pre-equilibrated Protein-A affinity column (GE, USA, Cat#: 17040501, Lot no.: 10252250) and eluted with elution buffer (20 mM citric acid, pH3.0-pH3.5). Then, antibodies were kept in PBS buffer (pH 7.0), and their concentrations were determined using a NanoDrop instrument.

The isotype of each purified antibody was identified by using the Rapid Isotyping Kit with Kappa and Lambda-Mouse (Thermal, USA, Cat#: 26179) and Mouse Monoclonal Antibody Isotyping Reagents (Sigma, USA, Cat#: IS02-1KT), following the manufacturer's manuals. The isotyping results and the expression titer of the selected top 33 clones were summarized in Table 3.

TABLE 3

Isotype and expression titer of anti-OD40 antibodies

| Clone | Isotype | Expression Titer (mg/L) |
|---|---|---|
| 69A9 | IgG1κ | 2.6 |
| 26D9 | IgG2bκ | 22 |
| 68C8 | IgG1κ | 12.2 |
| 6A12 | IgG1κ | 4.3 |
| 71H8 | IgG1κ | 11.3 |
| 96B9 | IgG1κ | 1.0 |
| 190A7 | IgG1κ | 13.547 |
| 118D7 | IgG2bκ | 11.756 |
| 143D6 | IgG1κ | 1.929 |
| 185A12 | IgG2aκ | 14.190 |
| 134G4 | IgG2aκ | 2.318 |
| 192E4 | IgG1κ | 1.135 |
| 186G4 | IgG1κ | 2.150 |
| 137A12 | IgG2aκ | 33.978 |
| 147H2 | IgG1κ | 10.967 |
| 136B8 | IgG2aκ | 26.433 |
| 118A7 | IgG2aκ | 31.311 |
| 204F7 | IgG2b,κ | 8.568 |
| 285A2 | IgG2a,κ | 2.184 |
| 276F12 | IgG2a,κ | 4.264 |
| 299B3 | IgG1,κ | 4.908 |
| 222A11 | IgG1,κ | 11.450 |
| 295D8 | IgG1,κ | 6.850 |
| 262F2 | IgG1,κ | 10.900 |
| 295D8 | IgG1,κ | 19.200 |
| 279H4 | IgG2a,κ | 5.250 |
| 253 E9 | IgG1,κ | 3.064 |
| 270 E9 | IgG1,κ | 22.836 |
| 278G9 | IgG1,κ | 2.501 |
| 253G5 | IgG2a,κ | 5.302 |
| 287G7 | IgG2a,κ | 6.720 |
| 274F1 | IgG2a,κ | 7.248 |
| 268D2 | IgG2a,κ | 4.308 |

Example 4 Purified Anti-OX40 Monoclonal Antibodies Bound to Human and Monkey OX40

Purified anti-OX40 monoclonal antibodies were firstly characterized by ELISA assays to determine their binding affinities to recombinant human, monkey or mouse OX40 proteins.

ELISA plates were coated with 500 ng/ml human OX40-his (used in Example 2) at 4° C. overnight. The wells were blocked with 200 µl of blocking buffer (PBS containing 1% BSA, 1% goat serum, 0.05% Tween 20) for 2 hours at room temperature, and then 100 µl of serially diluted anti-OX40 antibodies (starting from 40 µg/ml) were added to each well and incubated for 1 hour at RT. Plates were washed for 3 times with PBST (PBS+0.05% Tween 20), added with Goat-anti-mouse IgG-HRP (Simga, US, Cat#: A9309-1 ml) diluted 5000×, and incubated for 1 hour at RT. Plates were developed with freshly prepared Ultra-TMB (BD, US, Cat#: 555214) for 5 minutes at RT. Absorbance was read on a SpectraMax® i3× (Molecular Devies, US) at 450 nm.

Species-cross-reactivity of the 33 OX40 mAbs to monkey or mouse OX40 was further assessed by direct ELISA. Briefly, 500 ng/ml monkey OX40-his or mouse OX40-his (used in Example 2) was coated on 96-well ELISA plates followed by incubation with 100 µl of serially diluted anti-OX40 antibodies (starting from 40 µg/ml). Goat anti-mouse IgG (Sigma, US, Cat#:A9309-1 ml) conjugated with HRP was used then. MEDI0562 and RG7888, the reference anti-OX40 antibodies, having human IgG1/kappa constant regions, were prepared using the amino acids sequences disclosed in patent application US2016/0137740A1 and WO2015/15 3513 A1, respectively.

$EC_{50}$ values for these binding tests were summarized in Table 4. It can be seen that all the 33 antibodies clearly cross-reacted with monkey OX40 but not mouse OX40.

TABLE 4

Binding capacity of 33 Anti-OX40 mAbs to human, monkey or mouse OX40

| | $EC_{50}$ (ng/ml) | | |
|---|---|---|---|
| Clone | hOX40-his | rhOX40-his | muOX40-his |
| 69A9 | 55.18 | 62.88 | N/A |
| 26D9 | 23.91 | 61.05 | N/A |
| 68C8 | 48.32 | 60 | N/A |
| 6A12 | 41.46 | 49.98 | N/A |
| 71H8 | 51.95 | 50.12 | N/A |
| 96B9 | 115 | 101.1 | N/A |
| 190A7 | 60.86 | 33.65 | N/A |
| 118D7 | 322.3 | 25508 | N/A |
| 143D6 | 127.4 | 46.03 | N/A |
| 185A12 | 30.67 | 21.93 | N/A |
| 134G4 | 132.4 | 47.6 | N/A |
| 192E2 | 57.73 | 278.1 | N/A |
| 186G4 | 55.31 | 31.17 | N/A |
| 137A12 | 1606 | 309.6 | N/A |
| 147H2 | 61.06 | 42.48 | N/A |
| 136B8 | 76.48 | 49.29 | N/A |
| 118A7 | 54.37 | 25.2 | N/A |
| 204F7 | 20.08 | 22.41 | N/A |
| 285A2 | 51.48 | 79.02 | N/A |
| 276F | 59.14 | 79.42 | N/A |
| 299B3 | 32.51 | 41.65 | N/A |
| 222A11 | 26.77 | 25.9 | N/A |
| 295E10 | 31.51 | 30.05 | N/A |
| 262F2 | 28.82 | 30.79 | N/A |
| 295D8 | 48.74 | 49.93 | N/A |
| 279H4 | 54.55 | 80.48 | N/A |
| 253E9 | 50.79 | 72.38 | N/A |
| 270E9 | 32.73 | 38.86 | N/A |

TABLE 4-continued

Binding capacity of 33 Anti-OX40 mAbs to human, monkey or mouse OX40

| Clone | $EC_{50}$ (ng/ml) | | |
|---|---|---|---|
| | hOX40-his | rhOX40-his | muOX40-his |
| 278G9 | 23.42 | 23.3 | N/A |
| 253G5 | 26.72 | 30.41 | N/A |
| 287G7 | 27.48 | 28.59 | N/A |
| 274F1 | 49.1 | 82.58 | N/A |
| 268D2 | 37.59 | 51.53 | N/A |
| MEDI0562 | 65.14 | 54.57 | N/A |
| RG7888 | 63.71 | 66.77 | N/A |

Example 5 Anti-OX40 Monoclonal Antibodies Bound to Human and Rhesus OX40 Expressed on HEK293A Cells To further determine whether anti-OX40 antibodies bound to human, monkey or mouse OX40 expressed on HEK293A cells, a cell-based binding assay by FACS was performed using the HEK293A cells stably overexpressing human, monkey or mouse OX40 (see Example 1), respectively. Briefly, $10^5$ HEK293A cells were seeded into each well of the 96-well plates and serially diluted anti-OX40 antibodies were added to the plates. After incubated at 4° C. for 1 hour, plates were washed 3 times with PBST. Then, an APC coupled Goat Anti-Mouse IgG (BioLegen, US, Cat#: 405308) diluted 500× was added to the plates. After incubation at 4° C. for 1 hour, the plates were washed with PBS for 3 times and then cell fluorescence was monitored using a FACS machine (BD). As shown in Table 5 below, all of the 33 anti-OX40 monoclonal antibodies showed high binding capacity to both human and rhesus monkey OX40 but did not bind to mouse OX40 (data not shown).

TABLE 5

Binding affinity of anti OX-40 antibodies to human and monkey OX40

| Clone | $EC_{50}$ (ng/ml) | |
|---|---|---|
| | HEK-293A/h OX40 | HEK-293A/Rh OX40 |
| 69A9 | 43.69 | 40.32 |
| 26D9 | 97.75 | 73.75 |
| 68C8 | 112.5 | 95.04 |
| 6A12 | 405.5 | 253 |
| 71H8 | 112.9 | 125.7 |
| 96B9 | 227.2 | 217 |
| 190A7 | 61.4 | 33.04 |
| 118D7 | 86.27 | 59.65 |
| 143D6 | 55.91 | 25.46 |
| 185A12 | 88.51 | 54.43 |
| 134G4 | 102.9 | 41.83 |
| 192E2 | 53.05 | 26.42 |
| 186G4 | 99.05 | 28.89 |
| 137A12 | 87.3 | 155.9 |
| 147H2 | 59.01 | 23.12 |
| 136B8 | 90.46 | 110.4 |
| 118A7 | 88.4 | 35.64 |
| 204F7 | 83.91 | 54.06 |
| 285A2 | 119.7 | 86.26 |
| 276F | 57.47 | 99.05 |
| 299B3 | 37.75 | 39.7 |
| 222A11 | 89.75 | 46.58 |
| 295E10 | 98.77 | 35.83 |
| 262F2 | 60.91 | 23.41 |
| 295D8 | 65.8 | 24.78 |

TABLE 5-continued

Binding affinity of anti OX-40 antibodies to human and monkey OX40

| Clone | $EC_{50}$ (ng/ml) | |
|---|---|---|
| | HEK-293A/h OX40 | HEK-293A/Rh OX40 |
| 279H4 | 85.85 | 128.6 |
| 253E9 | 46.14 | 59.99 |
| 270E9 | 30.26 | 32.73 |
| 278G9 | 57.97 | 19.3 |
| 253G5 | 74.11 | 89.72 |
| 287G7 | 95.92 | 56.41 |
| 274F1 | 74.03 | 75.84 |
| 268D2 | 36.78 | 50.5 |
| MEDI0562 | 93.47 | 88.04 |
| RG7888 | 133.8 | 112.8 |

Example 6 Anti-OX40 Antibodies Inhibited Human OX40-OX40L Interaction

Purified anti-human OX40 antibodies were further analyzed for their ability of blocking binding of human OX40L to human OX40. Briefly, 96-well ELISA plates were coated with 500 ng/ml human OX40-his (used in Example 2) at 4° C. overnight. The plates were blocked with 200 μl of blocking buffer (PBS+2% BSA) for 2 hours at room temperature. Then serially diluted anti-OX40 antibodies (starting from 40 μg/ml) were added into the wells and incubated at RT for 1 hour, followed by addition of 100 μl of 2 μg/ml human OX40L-hFc (Sino biological, China, Cat#:13127-H01H). After incubated at RT for 1 hour, the plates were washed 3 times with PBST (PBS+0.05% Tween20) and then anti-Human IgG FC-HRP (1:5000, Sigma, USA, Cat#: A0170-1ML) was added to each well and incubated at room temperature for 1 hour. Plates were washed 3 times with PBST and then 80 μl of TMB was added to each well. Five to ten min later, 80 μl of 0.16 M sulfuric acid was added to each well and then OD450 was measured on a SpectraMaxR i3x (Molecular Devies, US).

Figure 2:
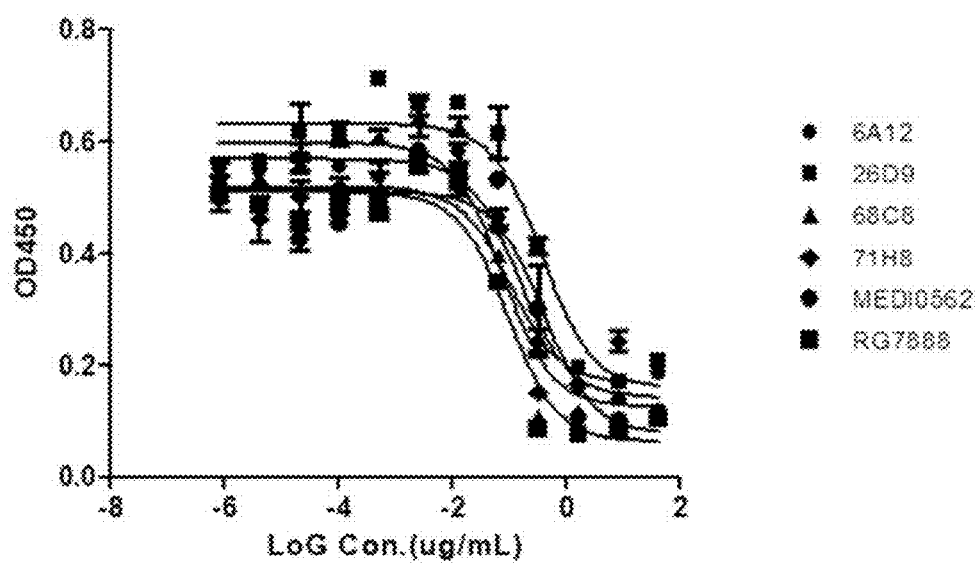
FIG. 2 shows the inhibitory effect of anti-OX40 antibodies on OX40/OX40L interaction.

Results of 4 representative clones were shown in FIG. 2. All the antibodies (6A12, 26D9, 68C8 and 71H8) blocked human OX40-OX40L interaction, and the binding of OX40 to OX40L (OD450 values) decreased along with the increasing concentration of anti-OX40 antibodies. MEDI0562 and RG7888 were used here as positive controls.

Example 7 Determination of Agonistic Activity of Anti-OX40 Antibodies

To determine whether the selected anti-OX40 antibodies had agonistic activity, a HEK-Blue activity assay was performed. Briefly, the HEK-Blue/OX40 cells, generated in Example 2, were incubated in DMEM medium (Hyclone, USA, Cat#: SH30243.01)+10% FBS (Excell, China, Cat#: FND500)+10 μg/ml Puromycin (GIBCO, USA, Cat#: A11138-03)+100 μg/ml Normocin™ (Invivogen, USA, Cat#: ant-nr-2)+100 μg/ml Zeocin (Invivogen, USA, Cat#: ant-Zn-5). Forty-thousand (40,000) HEK-Blue/OX40 cells were suspended in 200 μl of culture medium in each well of the 96-well assay plate and cultured at 37° C. After overnight incubation (~12 hour), 200 μl of fresh DMEM medium was used to replace the culture medium. Seven hours later, the DMEM medium in each well was replaced with 100 μL/well of HEK Blue Detection buffer (Invivogen; USA; Cat#: hb-det3) containing anti-OX40 antibodies at various concentration (from 100 μg/ml to 0.002 ng/ml). The cells were incubated at 37° C. until appropriate blue color developed. Absorbence at 650 nm was measured using a SpectraMax microplate reader (Molecular Devices, US, SpectraMaxR i3X). MEDI0562 and RG7888 were used here as positive controls.

Figure 3:
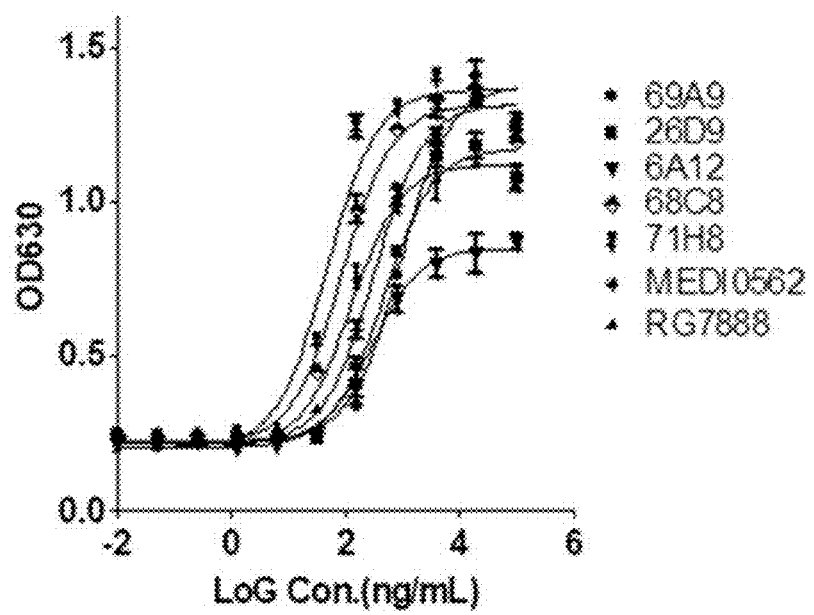
FIG. 3 shows the agonistic activity of anti-OX40 antibodies.

The 33 antibodies displayed different levels of agonistic activities in the functional HEK-Blue assays. $EC_{50}$ values were summarized in Table 6 below, and the agonistic activity of representative monoclonal antibodies was shown in FIG. 3. Several antibodies, such as 68C8 and 71H8, had lower $EC_{50}$ values and thus higher agonictiv activity than the two controls.

TABLE 6

Agonistic activity of anti-OX40 antibodies

| Antibody | $EC_{50}$ (ng/mL) |
|---|---|
| 69A9 | 860.3 |
| 26D9 | 469.1 |
| 68C8 | 86.59 |
| 6A12 | 273.8 |
| 71H8 | 49.38 |
| 96B9 | 395.8 |
| 190A7 | 46.52 |
| 118D7 | 107.2 |
| 143D6 | 56.25 |
| 185A12 | 80.32 |
| 134G4 | 919.6 |
| 192E2 | 47.13 |
| 186G4 | 71.37 |
| 137A12 | 256.1 |
| 147H2 | 41.32 |
| 136B8 | 1179 |
| 118A7 | 118.2 |
| 204F7 | 408.4 |
| 285A2 | 518.1 |
| 276F | 3251 |
| 299B3 | 436.7 |
| 222A11 | 141.8 |
| 295E10 | 98.03 |
| 262F2 | 105.8 |
| 295D8 | 99.54 |
| 279H4 | 3076 |
| 253E9 | 325 |
| 270E9 | 227.4 |
| 278G9 | 76.3 |
| 253G5 | 131.6 |
| 287G7 | 209.8 |
| 274F1 | 905.5 |
| 268D2 | 13400 |
| MEDI0562 | 309.9 |
| RG7888 | 120.6 |

Example 8 Epitope Binning

For epitope binning, a competition ELISA assay was used. Briefly, 96-well plates were coated with 5 μg/ml MEDI0562 or RG7888 at 4° C. overnight. The wells were blocked with 200 μl of blocking buffer (PBS containing 1% BSA, 1% goat serum, 0.05% Tween 20) for 2 hours at room temperature. Human OX40-His (Sino Biological, CN, Cat#: 10481-H03H) was diluted to 0.5 μg/mL and added to the plate, and then incubated for 1 hour at RT. The ELISA plates were washed for 3 times with PBST, and then the purified antibodies were diluted to 1 μg/mL and added to each well and allowed to incubate for 1 hour at RT. The ELISA plates were washed for 3 times with PBST, and then anti-mouse Fc-HRP (Sigma, US, Cat#: A9309-1MC) diluted at 1:20000 was added to each well and incubated for 1 hour at RT. Plates were developed with freshly prepared Ultra-TMB (Huzhou Yingchuang, CN, Cat#: TMB-S-003) for 5 minutes at RT and the absorbance was measured on a Thermo Multiscan FC at 450 nm (OD450).

The results were summarized in Table 7. Antibody 68C8 and 71H8, the two having the highest agonist activity, may bind the same or similar epitope as MEDI0562-hFc and RG7888-hFc.

TABLE 7

Epitope binning by competition ELISA

| Antibody | Binning | |
|---|---|---|
|  | MEDI0562 | RG7888 |
| 69A9 | Y | Y |
| 26D9 | N | N |
| 68C8 | Y | Y |
| 6A12 | N | N |
| 71H8 | Y | Y |
| 96B9 | Y | N |
| 190A7 | N | N |
| 118D7 | N | N |
| 143D6 | N | N |
| 185A12 | N | N |
| 134G4 | N | N |
| 192E2 | N | N |
| 186G4 | N | N |
| 137A12 | N | N |
| 147H2 | N | N |
| 136B8 | N | N |
| 118A7 | N | N |
| 204F7 | N | Y |
| 285A2 | N | Y |
| 276F | Y | N |
| 299B3 | N | N |
| 222A11 | N | N |
| 295E10 | N | N |
| 262F2 | N | N |
| 295D8 | N | N |
| 279H4 | N | N |
| 253E9 | N | N |
| 270E9 | N | N |
| 278G9 | Y | N |
| 253G5 | N | Y |
| 287G7 | N | N |
| 274F1 | N | N |
| 268D2 | N | N |

Y: with competition;
N: without competition

Example 9 Agonistic Anti-OX40 Antibodies Promoted T Cell Co-Stimulation

To further determine the agonistic activity of the anti-OX40 antibodies, a primary human T cell co-stimulation assay was performed. Briefly, PBMCs from the blood samples of two healthy human donors were collected by density gradient centrifugation. CD4+ memory T cells were isolated from the PBMCs using Invitrogen Dynabeads Untouched Human CD4+ T cells isolation kit (Thermal Fisher Scientific, USA, Cat#: 11346D) according to the manufacturer's instructions.

CD4+ T cells were suspended in complete RPMI culture medium and the cell density was adjusted to $1.0 \times 10^6$/ml. Phytohemagglutinin-leucoagglutinin (PHA-L) (sigma, Cat#: L1668-5MG) and recombinant human IL-2 (R&D, Cat#: 202-IL) were added with final concentrations of 2 μg/ml and 20 IU/ml, respectively, and cells were cultured at 37° C. under 5% $CO_2$ in a humidified tissue culture incubator for 2 days to activate T cells and upregulate OX40.

Above activated human CD4+ T cells were collected and washed in complete RPIM medium for 3 times, and the cell density was adjusted to 2×10⁵ viable cells/ml. Plates were pre-coated with 5 µg/ml anti-CD3 antibodies (OKT3, Sino Biological Inc. China, Cat#:GMP-10977-H001) and serially diluted anti-OX40 antibodies overnight at 4° C. The plates were washed with PBS and blocked for 90 minutes at 37° C. with 1% BSA in PBS. The plates were washed with PBS, and 150 µl of above CD4+ T cells (30000/well) were added to each well. Cells in the plates were incubated at 37° C. for 3 days, and then 100 µl of cell culture supernatant was used for IL-2 secretion measurement by using IL-2 detection kit (R&D, US). Two reference antibodies, MEDI0562 and RG7888, two known agonistic OX40 antibodies, were used as positive controls. An anti-HEL antibody (LifeTein, LLC, US, Cat. #:LT12031) was used as a negative control.

Figure 4A:
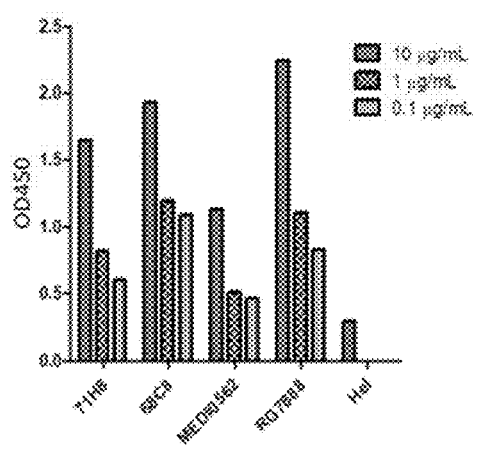
FIGS. 4A and 4B show the anti-OX40 antibodies' involvement in T cell costimulation where PBMCs were obtained from Donor 1 (A) and Donor 2 (B).
Figure 4B:
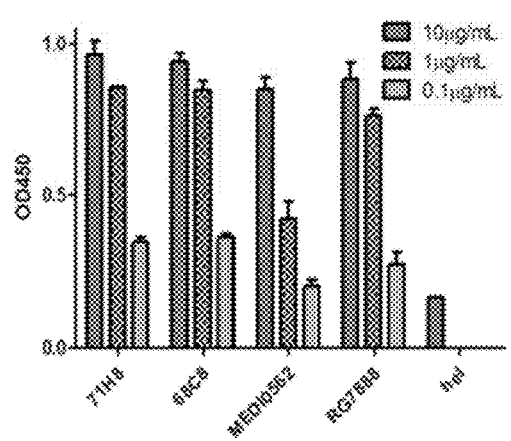
Figure 9A:
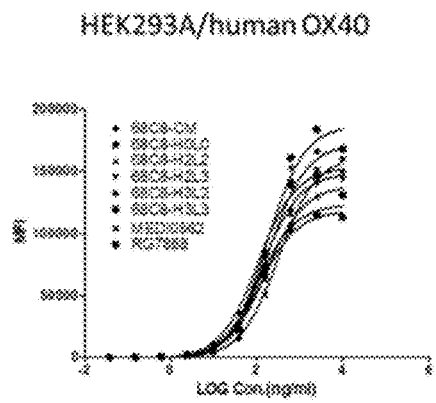
FIG. 9A-9D show the binding capacity of humanized anti-OX40 antibodies to human or monkey OX40 on HEK293A cell surfaces. Antibody 68C8 and its humanized versions bound to human (A) and monkey OX40 (B) on cell surfaces, and antibody 71H8 and its humanized versions bound to human (B) and monkey OX 40 (D) on cell surfaces.
Figure 9B:
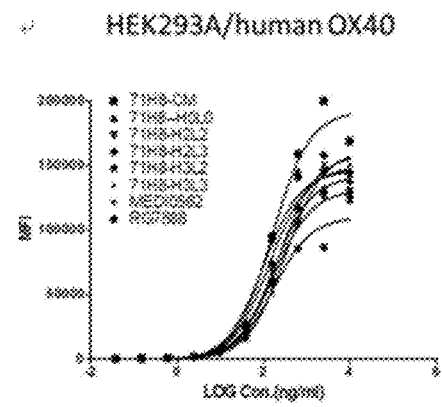
Figure 9C:
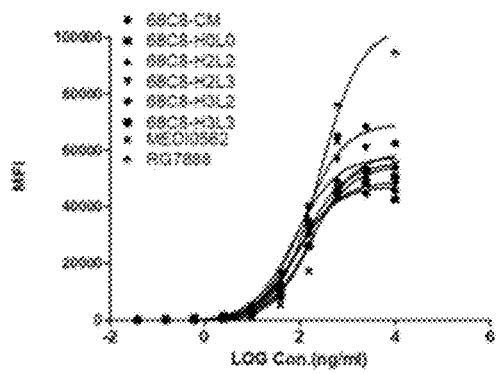
Figure 9D:
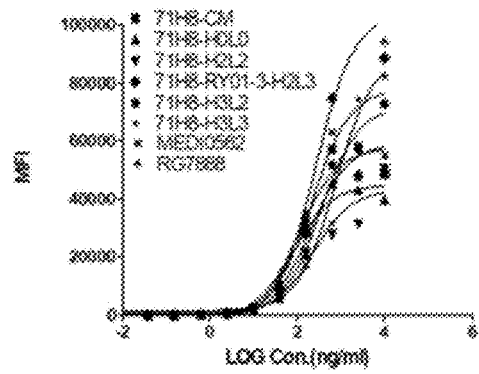

As shown in FIGS. 4A and 4B, monoclonal antibody 71H8 and 68C8 promoted T cell co-stimulation and increased IL-2 secretion in a dose dependent manner.

Example 10 Expression and Purification of Chimeric Anti-OX40 Antibodies

Three antibodies (6A12, 71H8 and 68C8) were selected for further tests. The variable region sequences of the 3 selected candidate antibodies were cloned from hybridoma cells using the standard PCR method with a set of degenerated primers as describes in literatures (Juste et al., (2006), *Anal Biochem.*, 1; 349(1):159-61). Expression vectors were constructed by inserting the sequences encoding the variable region sequences plus respective human IgG1/kappa constant region sequences (amino acid sequences of heavy chain constant region and light chain constant region set forth in SEQ ID NOs: 29 and 30, respectively) into XhoI/BamHI restriction sites of pCDNA3.1 (Invitrogen, Carlsbad, USA). The amino acid SEQ ID numbers of variable regions were summarized in Table 1 above.

The expression vectors were PEI transfected into HEK-293F cells (Cobioer, N.J., China). In specific, HEK-293F cells were cultured in Free Style™ 293 Expression Medium (Gibco, Cat#: 12338-018) and transfected with the expression vectors using polyethyleneinimine (PEI) at a DNA:PEI ratio of 1:3, 1.5 µg of DNAs per millimeter of cell medium. Transfected HEK-293F cells were cultured in an incubator at 37° C. under 5% $CO_2$ with shaking at 120 RPM. After 10-12 days, supernatants were harvested and monoclonal antibodies were purified as described in Example 3.

Example 11 Chimeric Anti-OX40 Monoclonal Antibodies Bound to Human or Rhesus Monkey OX40 Expressed on HEK293A Cells The 3 chimeric anti-OX40 antibodies were further characterized for their ability of binding to HEK293A/huOX40 cells and HEK293A/rhOX40 cells as generated in Example 1, according to the protocol of Example 5.

As shown in FIGS. 5A and 5B, the chimeric antibodies had high binding affinity to both human and monkey OX40. The $EC_{50}$ of chimeric antibodies 6 A12, 71H8 and 68C8 to HEK293A/huOX40 cells were 177.1 ng/ml, 144 ng/ml and 133.9 ng/ml, respectively, while their binding $EC_{50}$ to HEK293A/rh OX40 cells were 882.7 ng/ml, 151.3 ng/ml and 80.65 ng/ml, respectively.

Example 12 Chimeric Anti-OX40 Monoclonal Antibodies had Angonist Activity and Promoted T Cell Co-Stimulation The chimeric antibodies were assayed for their effect on OX40 signaling activation and T cell co-stimulation, following the protocols described in Example 7 and Example 9. As shown in FIG. 6 and FIG. 7, the 3 chimeric antibodies displayed similar functional activities as their parent monoclonal antibodies.

Example 13 Humanization of Anti-OX40 Antibodies

Based on the characterizations and assays described above, two candidate antibodies, 68C8 and 71H8, were selected for humanization and further investigations. Humanization of the murine antibodies was conducted using the well-established CDR-grafting method (U.S. Pat. No. 5,225,539, incorporated herein by reference in its entirety) as described in detail below.

To select acceptor frameworks for humanization of murine antibodies 68C8 and 71H8, the light and heavy chain variable chain sequences of 68C8 and 71H8 were blasted against the human immunoglobulin gene database in NCBI website (http://www.ncbi.nlm.nih. gov/igblast/). The human germline IGVH and IGVK with the highest homology to 68C8 and 71H8 were selected as the acceptor for humanization. For antibody 68C8 and 71H8, the human heavy chain acceptor selected was IGHV1-46*01, and the human light chain acceptor selected was IGKV1-33*01.

The three dimensional structures were simulated for variable domains of 68C8 and 71H8 in order to identify key framework residues that might be playing important roles in supporting CDR loop structures, thus designing back mutations in humanized antibodies. Selected structure templates had the same classes of canonical loop structures in L-CDR1, L-CDR2, L-CDR3, H-CDR1, H-CDR2 and H-CDR3 to 68C8 and 71H8, respectively. Using the structural templates selected, structural models were built by replacing the murine frameworks with human acceptor's frameworks for heavy and light chains. Three-dimensional structural modeling simulation was then performed to identify key framework residues that might be important in supporting the CDR-loop structures or the heavy and light chain interface. When the murine antibody and the human acceptor shared the same residue at a certain site in the framework, the human germline residue was kept. On the other hand, when the murine antibody and human germline acceptor had a different residue at a certain site in the framework, the importance of this residue was evaluated by structural modeling. If a residue in the murine antibody's framework was found to interact with and influence the CDR residues, then this residue was back-mutated to murine residue.

TABLE 8

Structural templates used in antibody structure simulations

| Antibody chain | PDB code of template structure | Sequence identity | Sequence similarity |
|---|---|---|---|
| 68C8 Heavy chain | 1WT5 | 72% | 84% |
| 68C8 Light chain | 2FGW | 84% | 92% |
| 71H8 Heavy chain | 1WT5 | 73% | 85% |
| 71H8 Light chain | 2FGW | 81% | 90% |

Based on the structural modeling as described above, 5 potential back-mutations (A40R, K43Q, M48I, M70L, E72V) were identified for heavy chain and 4 potential back-mutations (A43T, P44V, F71Y, Y87F) for light chain of 68C8. For 71H8, 6 potential back-mutations (D27Y, A40R, K43Q, M48I, M70L, E72V) were identified for heavy chain and 4 back-mutations (A43T, P44V, F71Y, Y87F) were identified for light chain.

As summarized in Table 1, for 68C8, three humanized heavy chain variable regions and three humanized light chain variable regions were designed, with a total of 5 humanized antibodies. Similarly, for 71H8, three humanized heavy chain variable regions and three humanized light chain variable regions were designed, with a total of 5 humanized antibodies.

The sequences encoding the humanized heavy and light chain variable regions plus human IgG1/kappa constant region sequences were chemically synthesized and then subcloned into the pcDNA3.1(+)-based expression vector (Invitrogen, USA) using the BamH I and Xho I restriction sites. All expression constructs were confirmed by DNA sequencing. The HEK293F expression systems (Invitrogen, USA) were transfected with vectors and transiently expressed 10 humanized anti-OX40 antibodies (5 for 71H8, and 5 for 68C8), according to the protocol described in Example 10. The humanized antibodies were purified as described in Example 3.

Example 14 Humanized Anti-OX40 Antibodies Bound to Human or Rhesus OX40

The humanized anti-OX40 antibodies were further characterized for their ability of binding to human, rhesus or mouse OX40 by ELISA assay, following the protocols described in Example 2.

As shown in FIG. 8A-8F, all the humanized anti-OX40 antibodies retained their binding affinity to both human and rhesus OX40, but did not bind to murine OX40, as their parent murine and chimeric antibodies.

Example 15 Humanized Anti-OX40 Antibodies Bound to Human or Rhesus OX40 Expressed on HEK293A Cells The humanized anti-OX40 antibodies were also tested for their ability of binding to HEK293A/huOX40 cells or HEK293A/rhOX40 cells, following the FACS analysis protocol as described in Example 5.

As shown in FIG. 9A-9D, all the humanized anti-OX40 antibodies showed their high affinity to both HEK/293A human OX40 cells and HEK293A/rhesus OX40 cell, as their parent murine and chimeric antibodies.

Figure 10A:
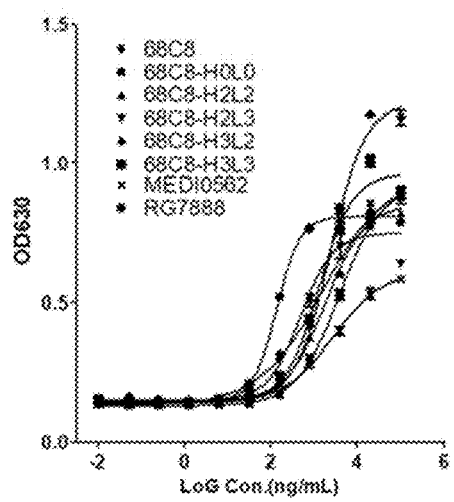
FIGS. 10A and 10B show the agonistic activity of antibody 68C8 and its humanized versions (A), as well as antibody 71H8 and its humanized versions (B).
Figure 10B:
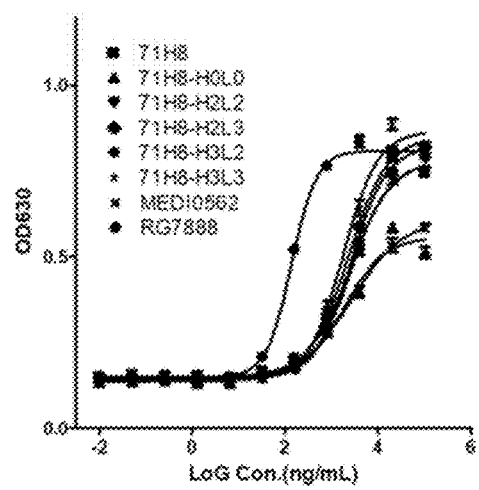

Example 16 Humanized Anti-OX40 Antibodies Showed Agonistic Activity to OX40 Signaling The humanized antibodies were also assayed for their ability to activate OX40 signaling in the HEK-Blue assay as described in Example 7. Two reference antibodies, RG7888 and MEDI0562 were used as positive controls. As shown in FIGS. 10A and 10B, all the humanized anti-OX40 antibodies activated OX40 signaling.

Example 17 Humanized Antibodies Promoted T Cell Co-Stimulation

The humanized antibodies were further analyzed for their involvement in T cell co-stimulation, following the protocol described in Example 9. In addition to IL-2 secretion, the effect of anti-OX40 antibodies on CD4+ T cell proliferation was also studied.

Human primary pre-activated (by PHA and IL-2) CD4+ T cells isolated from bloods of two healthy human donors were labeled with carboxyflueorescein succinimidyl ester (CFSE, Invitrogen, USA, Cat#: C34554), according to the manufacturer's instructions, except that 2.5 µM CFSE was used and the incubation was performed for 10 minutes at 37° C. After labeling, cells were suspended in complete RPMI medium (RPMI medium+10% FBS) and the cell density was adjusted to $1.5 \times 10^5$ viable cells/ml. The plates were pre-coated with 5 µg/ml anti-CD3 antibodies (OKT3, Sino Biological Inc. China, Cat#: GMP-10977-H001) and serially diluted anti-OX40 antibodies overnight at 4° C. The plates were washed with PBS and blocked for 90 minutes at 37° C. with 1% BSA in PBS. The plates were washed with PBS, and 150 µl of CD4+ T cells (30000/well) were added to each well. Cells were incubated at 37° C. for 3 days, and then sent to FACS analysis. Anti-OX40 antibodies RG7888 and MEDI0562 as well as an anti-HEL antibody (LifeTein, LLC, US, Cat. #:LT12031) were used as controls. As shown in FIGS. 11A and 11B and FIGS. 12A and 12B, all the humanized anti-OX40 antibodies enhanced T cell activity, and increased IL-2 secretion and promoted T cell proliferation in a dose dependent manner.

Example 18 Affinity of Chimeric or Humanized Anti-OX40 Antibodies to Human OX40

SPR assays were used to determine the binding affinity of the chimetic or humanized anti-OX40 antibodies to human OX40 with the BIAcore™ 8K instrument (GE Life Sciences). Briefly, 100-200 response units (RU) of human OX40-His protein (Sino Biological, CN, Cat#:10481-H03H, Lot no.: MA08MA3003) were coupled to CM5 biosensor chips (Cat#: BR-1005-30, GE Life Sciences), followed by blocking of un-reacted groups with 1M ethanolamine. Serially diluted antibodies at concentrations ranging from 0.3 µM to 10 µM were injected into the SPR running buffer (HBS-EP buffer, pH7.4, GE Life Sciences; US; Cat#:BR-1006-69) at 30 µL/minute. The binding capacitity was calculated with the RUs of blank controls subtracted. The association rate ($k_a$) and dissociation rate ($k_d$) were calculated using the one-to-one Langmuir binding model (BIA Evaluation Software, GE Life Sciences). The equilibrium dissociation constant $K_D$ was calculated as the $k_d/k_a$ ratio. The SPR-determined binding curves of antibodies were shown in FIGS. 13A-13N, and the binding affinities of those chimeric or humanized antibodies were listed in Table 9. Anti-OX40 antibodies RG7888 and MEDI0562 were used as controls in this assay.

TABLE 9

Binding affinities of anti-OX40 antibodies to human OX40

| Antibodies | $k_a$ | $k_d$ | $K_D$ |
|---|---|---|---|
| MEDI0562 | 8.63E+4 | 1.54E-4 | 1.79E-9 |
| RG7888 | 3.22E+5 | 1.76E-6 | 5.49E-12 |
| 68C8 | 3.93E+5 | 7.35E-5 | 1.87E-10 |
| 68C8-H0L0 | 4.1E+5 | 1.84E-3 | 4.49E-9 |
| 68C8-H2L2 | 2.07E+5 | 1.05E-3 | 5.07E-9 |
| 68C8-H2L3 | 4.73E+5 | 9.27E-4 | 1.96E-9 |
| 68C8-H3L2 | 1.65E+5 | 1.57E-3 | 9.55E-9 |
| 68C8-H3L3 | 2.03E+5 | 8.21E-4 | 4.04E-9 |
| 71H8 | 5.25E+5 | 8.28E-5 | 1.58E-10 |
| 71H8-H0L0 | 2.97E+5 | 2.74E-3 | 9.21E-9 |
| 71H8-H2L2 | 3.58E+5 | 1.72E-3 | 4.81E-9 |
| 71H8-H2L3 | 4.34E+5 | 1.98E-3 | 4.57E-9 |
| 71H8-H3L2 | 2.34E+5 | 8.71E-3 | 3.72E-8 |
| 71H8-H3L3 | 3.25E+5 | 2.07E-3 | 6.36E-9 |

Example 19 Epitope Mapping of Humanized Anti-OX40 Antibodies

The humanized anti-OX40 antibodies were tested for their binding epitope by ELISA.

There are four individual cysteine enriched domains (CRD) in OX40 extracellular domain (ECD), namely CRD1, CRD2, CRD3 and CRD4, respectively. Based on the structure of OX40, four recombinant OX40 proteins were generated, i.e., the full-length OX40 ECD (containing CRD1/2/3/4) (SEQ ID NO.: 38), truncant 1-mFc (containing CRD2/3/4) (SEQ ID NO.: 39), truncant 2-mFc (containing CRD/3/4) (SEQ ID NO.: 40) and truncant 3-mFc (containing CRD/4) (SEQ ID NO.: 41). All the recombinant proteins were linked with a signal peptide (SEQ ID NO.: 42) at the N terminus for protein secretion and a mFc-tag (SEQ ID NO.: 43) at the C terminus for ELISA assay. DNA sequences were synthesized and subcloned into pcDNA3.1 vector. The expression and purification of the recombinant proteins were carried out according to the protocols in Example 10. ELISA assay was performed to assess binding capacity of mAbs to recombinant OX40 proteins, following the protocol in Example 2. Anti-OX40 antibodies RG7888 and MEDI0562 were used as controls.

Figure 14:
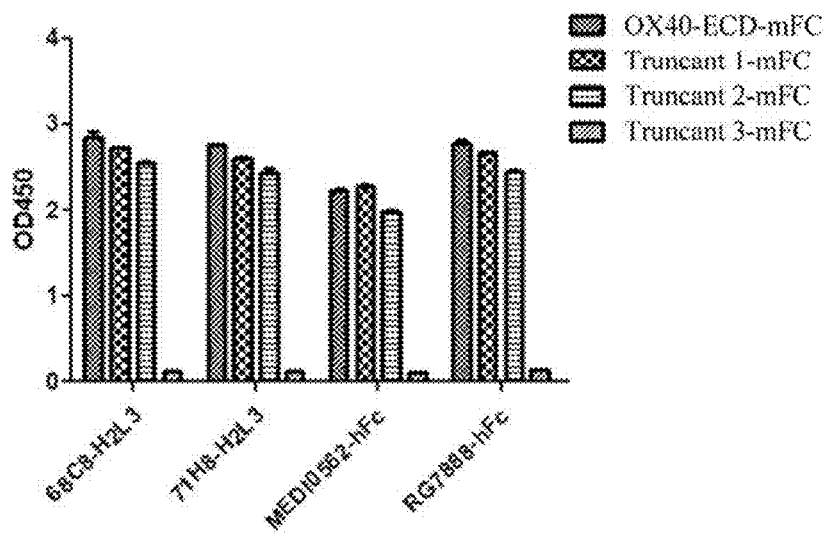
FIG. 14 shows the binding capacity of humanized anti-OX40 antibodies to four recombinant OX40 ECD proteins.

As shown in FIG. 14, all the antibodies bound to full length OX40 ECD-mFc, truncant 1-mFc and truncant 2-mFc, but not to truncant 3-mFc. The results indicated that antibodies 68C8H2L3 and 71H8 H2L3, along with the two reference antibodies, bound to the epitopes localized at CRD3/4.

Example 20 Humanized Anti-OX40 Antibodies Specifically Bound to Human OX40

ELISA assays were performed to determine the binding specificity of anti-OX40 antibodies to human OX40, in comparison to other human TNFRSF members with homologous amino acid sequences, following the protocol described in Example 2.

The binding affinities of anti-OX40 antibodies to human CD40-his (TNFRSF5, Sino Biological, China, Cat#:10774-H08H), human HVEM-mFc (TNFRSF14, ACRO, China, Cat#: HVM-H5255), human 4-1BB (TNFRSF9, ACRO, China, Cat#:41B-H522a), human NGFR (TNFRSF16, Sino Biological, China, Cat#: 13184-H08H), human DR6 (TNFRSF21, Sino Biological, China, Cat#: 10175-H08H), and human RANK(TNFRSF11, ACRO, China, Cat#:RAL-H5240) were studied.

Figures 15A, 15B:
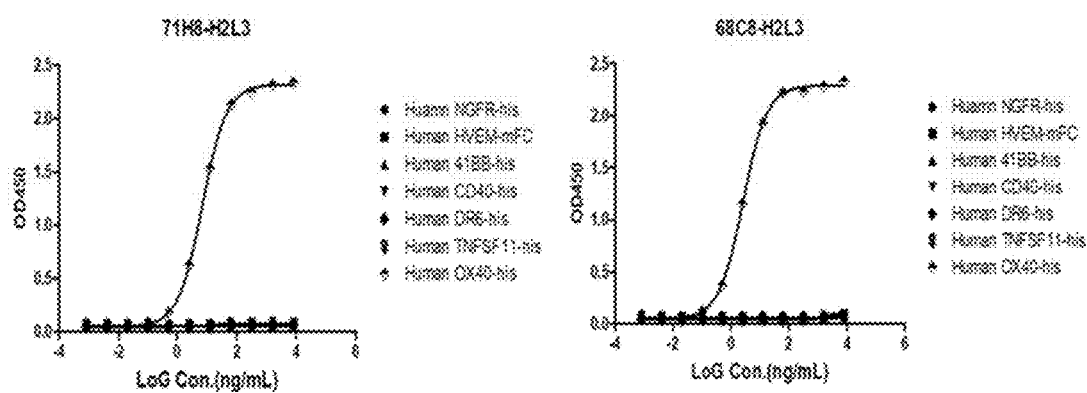
FIGS. 15A and 15B show the binding specificity of humanized anti-OX40 antibodies 71H8-H2L3 (A) and 68C8-H2L3 (B) to human OX40.

As shown in FIGS. 15A and 15B, neither 68C8-H2L3 nor 71H8-H2L3 showed binding to recombinant human CD40 (TNFRSF5), HVEM(TNFRSF14), 4-1BB(TNFRSF9), NGFR(TNFRSF16), DR6(TNFRSF21) or RANK (TNFRSF11), suggesting that 68C8-H2L3 and 71H8-H2L3 specifically bound to human OX40.

Example 21 Humanized Anti-OX40 Monoclonal Antibodies had In Vivo Anti-Tumor Effect In vivo anti-tumor activity of antibodies 68C8-H2L3 and 71H8-H2L3 were studied in an animal model established by grafting MC38 murine colon adenocarcinoma in transgenic mice with human OX40 (GemPharmatech Co. Ltd, China).

Each mouse was subcutaneously injected with $1 \times 10^6$ MC38 cells at one flank at day 0. When tumors grew to about 80 mm$^3$, the animals were randomly assigned into five groups, 8 mice per group. The animals were then i.p. administered with 68C8-H2L3, 71H8-H2L3, control antibodies or PBS at a dose of 10 mg/kg/day at Day 5, 8, 12, 15 and 18.

Tumor size was followed over time, with volumes measured every three days. Tumor measurements (width and length) were taken by caliper and tumor volume calculated by the formula TV=(length×width$^2$)/2. The experiment was terminated before the tumor volume in antibody administration groups reached 3.5 cm$^3$. One-way ANOVA was used to identify tumor volume differences.

At Day 20, four mice from each group were selected for T cell analysis, and the other mice were kept alive for tumor volume measurement still Day 60. The tumors were collected immediately after the mice were sacrificed and placed in Hanks buffer with collagenases. The tumors were then cut into small pieces and incubated in Hanks buffer with collagenases at 37° C. for 30 min with gentle shaking. Thereafter, 10 ml of RPMI 1640+10% FBS was added to each sample to deactivate the collagenase and maintain viability of the immune cells. Samples were passed through a 70 μm cell filter membrane (Corning, Cat#: 352350) and placed in new tubes. The samples were pelleted and resuspended in PBSF buffer (PBS+2% FBS) at a density of $1*10^7$ cells/ml. The samples were washed by PBSF buffer for 2 times, and added with anti-CD45 (Brilliant Violet 785 ™ anti-mouse CD45 Antibody; Biolegend; US; Cat#: 103149) and anti-CD8 (APC anti-mouse CD8a Antibody; Biolegend; US; Cat#: 100712) fluorescent antibody mixtures. The resultant mixtures were incubated for half an hour at 4° C. Cells were washed 2 times by PBSF buffer and analyzed on a FACS machine (BD)

As shown in FIG. 16A-16F, treatment with anti-OX40 antibodies resulted in significantly reduced tumor growth, as compared to negative control group, although individuals responded differently. Tumor growth inhibition was observed in all mice (in the group with 71H8H2L3 administration) or most mice (6 out of 8 in the group with 68C8H2L3 administration) even post antibody withhold. Further, in the group treated with antibody 71H8H2L3, complete regression (CR) were found in all of the 4 remaining mice at Day 60, while CR was observed in only half of the mice in the other antibody administration groups. In addition, as shown in FIG. 17, antibodies 71H8H2L3 and 68C8H2L3 both evidently increased CD8$^+$ CD45$^+$ cells.

While the invention has been described above in connection with one or more embodiments, it should be understood that the invention is not limited to those embodiments, and the description is intended to cover all alternatives, modifications, and equivalents, as may be included within the spirit and scope of the appended claims. All referenced cited herein are further incorporated by reference in their entirety.

We claim:

1. An isolated monoclonal antibody, or an antigen-binding portion thereof, binding to tumor necrosis factor receptor OX40, comprising
   1) a heavy chain variable region which in turn comprises a heavy chain CDR1 region, a heavy chain CDR2 region and a heavy chain CDR3 region, wherein the heavy chain CDR1 region, the heavy chain CDR2 region and the heavy chain CDR3 region comprise amino acid sequences of a) SEQ ID NOs: 1, 3 and 6, respectively; or (2) SEQ ID NOs: 1, 4 and 6, respectively; and
   2) a light chain variable region which in turn comprises a light chain CDR1 region, a light chain CDR2 region and a light chain CDR3 region, wherein the light chain CDR1 region, the CDR2 region and the CDR3 region comprise amino acid sequences of SEQ ID NOs: 8, 10 and 12, respectively.

2. The isolated monoclonal antibody, or the antigen-binding portion thereof, of claim 1, wherein the heavy chain variable region comprises an amino acid sequence of SEQ ID NOs: 14, 15, 17, 18, 19, 20, 21 or 22.

3. The isolated monoclonal antibody, or the antigen-binding portion thereof, of claim 1, wherein the light chain variable region comprises an amino acid sequence of SEQ ID NOs: 23, 24, 26, 27 or 28.

4. The isolated monoclonal antibody, or an antigen-binding portion thereof, of claim 1, wherein the heavy chain variable region and the light chain variable region comprise amino acid sequences of (1) SEQ ID NOs: 14 and 23, respectively; (2) SEQ ID NOs: 15 and 24, respectively; (3) SEQ ID NOs: 17 and 26, respectively; (4) SEQ ID NOs: 18 and 27, respectively; (5) SEQ ID NOs: 18 and 28, respectively; (6) SEQ ID NOs: 19 and 27, respectively; (7) SEQ ID NOs: 19 and 28, respectively; (8) SEQ ID NOs: 20 and 26, respectively; (9) SEQ ID NOs: 21 and 27, respectively; (10) SEQ ID NOs: 21 and 28, respectively; (11) SEQ ID NOs: 22 and 27, respectively; or (12) SEQ ID NOs: 22 and 28, respectively.

5. The isolated monoclonal antibody, or an antigen-binding portion thereof, of claim 4, comprising a heavy chain and a light chain, wherein the heavy chain comprises a heavy chain constant region having an amino acid sequence of SEQ ID NO: 29, linked to the heavy chain variable region, and wherein the light chain comprises a light chain constant region having an amino acid sequence of SEQ ID NO: 30, linked to the light chain variable region.

6. The isolated monoclonal antibody, or an antigen-binding portion thereof, of claim 5, comprising two heavy chains and two light chains interconnected by disulfide bonds.

7. The antibody, or the antigen-binding portion thereof, of claim 1, which (a) binds human or monkey OX40; (b) blocks OX40-OX40L interaction; (c) does not bind to mouse OX40; (d) promotes T cell costimulation; (e) promotes IL-2 secretion; (f) promotes CD8+ T cell proliferation.

8. The antibody, or the antigen-binding portion thereof, of claim 1, which is a mouse, human, chimeric or humanized antibody.

9. The antibody, or the antigen-binding portion thereof, of claim 1, which is an IgG1, IgG2 or IgG4 isotype.

10. A pharmaceutical composition comprising the antibody, or antigen-binding portion thereof, of claim 1, and a pharmaceutically acceptable carrier.

11. The pharmaceutical composition of claim 10, further comprising an anti-tumor agent.

12. A method for treating a cancer disease in a subject, comprising administering to the subject a therapeutically effective amount of the isolated monoclonal antibody, or the antigen-binding portion thereof, of claim 1, or the pharmaceutical composition of claim 10.

13. The method of claim 12, wherein the cancer disease is a solid or non-solid tumor.

14. The method of claim 12, wherein the cancer disease is selected from the group consisting of lymphoma, melanoma, sarcoma, colon cancer, breast cancer, glioma, head and neck squamous cell carcinoma, non-small cell lung cancer, and colon adenocarcinoma.

15. The method of claim 12, further comprising administering an immunostimulatory antibody, a costimulatory antibody, a chemotherapeutic agent, and/or an agent activating OX40 expression.

16. The method of claim 15, wherein the immunostimulatory antibody is selected from the group consisting of an anti-PD-1 antibody, an anti-PD-L1 antibody, an anti-LAG-3 antibody, an anti-TIM 3 antibody, an anti-STAT3 antibody, and an anti-ROR1 antibody.

17. The method of claim 15, wherein the costimulatory antibody is an anti-CD137 antibody or an anti-GITR antibody.

18. The method of claim 15, wherein the chemotherapeutic agent is epitubicin, oxaliplatin, and/or 5-fluorouracil.

19. The method of claim 15, wherein the agent activating OX40 expression is an unmethylated CpG oligonucleotide, phytohemagglutinin-leucoagglutinin, and/or IL-2.

* * * * *

SEQUENCE LISTING

<160> NUMBER OF SEQ ID NOS: 43

<210> SEQ ID NO 1
<211> LENGTH: 5
<212> TYPE: PRT
<213> ORGANISM: Artificial Sequence
<220> FEATURE:
<223> OTHER INFORMATION: 71H8.68C8-HV-CDR1

<400> SEQUENCE: 1

Ser Tyr Trp Ile Thr
1               5

<210> SEQ ID NO 2
<211> LENGTH: 5
<212> TYPE: PRT
<213> ORGANISM: Artificial Sequence
<220> FEATURE:
<223> OTHER INFORMATION: 6A12-HV-CDR1

<400> SEQUENCE: 2

Ser Ser Trp Met Asn
1               5

<210> SEQ ID NO 3
<211> LENGTH: 17
<212> TYPE: PRT
<213> ORGANISM: Artificial Sequence
<220> FEATURE:
<223> OTHER INFORMATION: 71H8-HV-CDR2

<400> SEQUENCE: 3

Asp Ile Tyr Pro Gly Ser Gly Ser Thr Asn Gln Asn Glu Lys Phe Lys
1               5                   10                  15

Ser

<210> SEQ ID NO 4
<211> LENGTH: 17
<212> TYPE: PRT
<213> ORGANISM: Artificial Sequence
<220> FEATURE:
<223> OTHER INFORMATION: 68C8-HV-CDR2

<400> SEQUENCE: 4

Asp Ile His Pro Gly Ser Gly Ser Thr Asn Asn Asn Glu Lys Phe Lys
1               5                   10                  15

Asn

<210> SEQ ID NO 5
<211> LENGTH: 17
<212> TYPE: PRT
<213> ORGANISM: Artificial Sequence
<220> FEATURE:
<223> OTHER INFORMATION: 6A12-HV-CDR2

<400> SEQUENCE: 5

Arg Ile Tyr Pro Gly Asp Gly Ile Thr Asn Tyr Asn Gly Asn Phe Lys
1               5                   10                  15

Gly

<210> SEQ ID NO 6
<211> LENGTH: 8
<212> TYPE: PRT
<213> ORGANISM: Artificial Sequence
<220> FEATURE:

```
<223> OTHER INFORMATION: 71H8, 68C8-HV-CDR3

<400> SEQUENCE: 6

Leu Arg Pro Tyr Tyr Phe Val Tyr
1               5

<210> SEQ ID NO 7
<211> LENGTH: 6
<212> TYPE: PRT
<213> ORGANISM: Artificial Sequence
<220> FEATURE:
<223> OTHER INFORMATION: 6A12-HV-CDR3

<400> SEQUENCE: 7

Glu Phe Ile Pro Leu Gly
1               5

<210> SEQ ID NO 8
<211> LENGTH: 11
<212> TYPE: PRT
<213> ORGANISM: Artificial Sequence
<220> FEATURE:
<223> OTHER INFORMATION: 71H8, 68C8-LV-CDR1

<400> SEQUENCE: 8

Arg Ala Ser Gln Asp Ile Ser Asn Tyr Leu Asn
1               5                   10

<210> SEQ ID NO 9
<211> LENGTH: 16
<212> TYPE: PRT
<213> ORGANISM: Artificial Sequence
<220> FEATURE:
<223> OTHER INFORMATION: 6A12-LV-CDR1

<400> SEQUENCE: 9

Arg Ser Ser Lys Ser Leu Leu His Ser Asn Gly Ile Thr Tyr Leu Tyr
1               5                   10                  15

<210> SEQ ID NO 10
<211> LENGTH: 7
<212> TYPE: PRT
<213> ORGANISM: Artificial Sequence
<220> FEATURE:
<223> OTHER INFORMATION: 71H8, 68C8-LV-CDR2

<400> SEQUENCE: 10

Tyr Thr Ser Arg Leu Leu Ser
1               5

<210> SEQ ID NO 11
<211> LENGTH: 7
<212> TYPE: PRT
<213> ORGANISM: Artificial Sequence
<220> FEATURE:
<223> OTHER INFORMATION: 6A12-LV-CDR2

<400> SEQUENCE: 11

Gln Met Ser Asn Leu Ala Ser
1               5

<210> SEQ ID NO 12
<211> LENGTH: 9
<212> TYPE: PRT
<213> ORGANISM: Artificial Sequence
<220> FEATURE:
<223> OTHER INFORMATION: 71H8, 68C8-LV-CDR3
```

<400> SEQUENCE: 12

Gln Gln Gly Asn Thr Leu Pro Leu Thr
1               5

<210> SEQ ID NO 13
<211> LENGTH: 9
<212> TYPE: PRT
<213> ORGANISM: Artificial Sequence
<220> FEATURE:
<223> OTHER INFORMATION: 6A12-LV-CDR3

<400> SEQUENCE: 13

Ala Gln Asn Leu Glu Leu Pro Trp Thr
1               5

<210> SEQ ID NO 14
<211> LENGTH: 117
<212> TYPE: PRT
<213> ORGANISM: Artificial Sequence
<220> FEATURE:
<223> OTHER INFORMATION: 71H8-HV

<400> SEQUENCE: 14

Gln Val Gln Leu Gln Gln Ser Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Trp Ile Thr Trp Val Lys Gln Arg Pro Gly Gln Gly Leu Glu Trp Ile
        35                  40                  45

Gly Asp Ile Tyr Pro Gly Ser Gly Ser Thr Asn Gln Asn Glu Lys Phe
    50                  55                  60

Lys Ser Lys Ala Thr Leu Thr Val Asp Thr Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Lys Leu Arg Pro Tyr Tyr Phe Val Tyr Trp Gly Gln Gly Thr Thr
            100                 105                 110

Leu Thr Val Ser Ser
        115

<210> SEQ ID NO 15
<211> LENGTH: 117
<212> TYPE: PRT
<213> ORGANISM: Artificial Sequence
<220> FEATURE:
<223> OTHER INFORMATION: 68C8-HV

<400> SEQUENCE: 15

Gln Val Gln Leu Gln Gln Ser Gly Ala Glu Leu Val Lys Pro Gly Ala
1               5                   10                  15

Ser Val Lys Met Ser Cys Lys Ala Ser Gly Asp Thr Phe Thr Ser Tyr
            20                  25                  30

Trp Ile Thr Trp Val Lys Gln Arg Pro Gly Gln Gly Leu Glu Trp Ile
        35                  40                  45

Gly Asp Ile His Pro Gly Ser Gly Ser Thr Asn Asn Asn Glu Lys Phe
    50                  55                  60

Lys Asn Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Tyr Cys

```
                85                  90                  95

Ala Lys Leu Arg Pro Tyr Tyr Phe Val Tyr Trp Gly Gln Gly Thr Thr
            100                 105                 110

Leu Thr Val Ser Ser
        115

<210> SEQ ID NO 16
<211> LENGTH: 115
<212> TYPE: PRT
<213> ORGANISM: Artificial Sequence
<220> FEATURE:
<223> OTHER INFORMATION: 6A12-HV

<400> SEQUENCE: 16

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ala Phe Ser Ser Ser
            20                  25                  30

Trp Met Asn Trp Val Lys Gln Arg Pro Gly Lys Gly Leu Glu Trp Ile
        35                  40                  45

Gly Arg Ile Tyr Pro Gly Asp Gly Ile Thr Asn Tyr Asn Gly Asn Phe
    50                  55                  60

Lys Gly Lys Ala Thr Leu Thr Ala Asp Lys Ser Ser Ser Thr Ala Tyr
65                  70                  75                  80

Met Gln Leu Ser Gly Leu Thr Ser Ala Asp Ser Ala Val Tyr Phe Cys
                85                  90                  95

Ala Arg Glu Phe Ile Pro Leu Gly Trp Gly Thr Gly Thr Thr Val Thr
            100                 105                 110

Val Ser Ser
        115

<210> SEQ ID NO 17
<211> LENGTH: 117
<212> TYPE: PRT
<213> ORGANISM: Artificial Sequence
<220> FEATURE:
<223> OTHER INFORMATION: 68C8-VH0

<400> SEQUENCE: 17

Gln Val Gln Leu Val Gln Ser Gly Ala Glu Val Lys Lys Pro Gly Ala
1               5                   10                  15

Ser Val Lys Val Ser Cys Lys Val Ser Gly Asp Thr Phe Thr Ser Tyr
            20                  25                  30

Trp Ile Thr Trp Val Arg Gln Ala Pro Gly Lys Gly Leu Glu Trp Met
        35                  40                  45

Gly Asp Ile His Pro Gly Ser Gly Ser Thr Asn Asn Asn Glu Lys Phe
    50                  55                  60

Lys Asn Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Leu Arg Pro Tyr Tyr Phe Val Tyr Trp Gly Gln Gly Thr Leu
            100                 105                 110

Val Thr Val Ser Ser
        115

<210> SEQ ID NO 18
<211> LENGTH: 117
```

```
<212> TYPE: PRT
<213> ORGANISM: Artificial Sequence
<220> FEATURE:
<223> OTHER INFORMATION: 68C8-VH2

<400> SEQUENCE: 18

Gln Val Gln Leu Val Gln Ser Gly Ala Glu Val Lys Lys Pro Gly Ala
1               5                   10                  15

Ser Val Lys Val Ser Cys Lys Val Ser Gly Asp Thr Phe Thr Ser Tyr
            20                  25                  30

Trp Ile Thr Trp Val Arg Gln Arg Pro Gly Lys Gly Leu Glu Trp Met
        35                  40                  45

Gly Asp Ile His Pro Gly Ser Gly Ser Thr Asn Asn Asn Glu Lys Phe
    50                  55                  60

Lys Asn Arg Val Thr Met Thr Val Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Leu Arg Pro Tyr Tyr Phe Val Tyr Trp Gly Gln Gly Thr Leu
            100                 105                 110

Val Thr Val Ser Ser
        115

<210> SEQ ID NO 19
<211> LENGTH: 117
<212> TYPE: PRT
<213> ORGANISM: Artificial Sequence
<220> FEATURE:
<223> OTHER INFORMATION: 68C8-VH3

<400> SEQUENCE: 19

Gln Val Gln Leu Val Gln Ser Gly Ala Glu Val Lys Lys Pro Gly Ala
1               5                   10                  15

Ser Val Lys Val Ser Cys Lys Val Ser Gly Asp Thr Phe Thr Ser Tyr
            20                  25                  30

Trp Ile Thr Trp Val Arg Gln Arg Pro Gly Gln Gly Leu Glu Trp Ile
        35                  40                  45

Gly Asp Ile His Pro Gly Ser Gly Ser Thr Asn Asn Asn Glu Lys Phe
    50                  55                  60

Lys Asn Arg Val Thr Leu Thr Val Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Leu Arg Pro Tyr Tyr Phe Val Tyr Trp Gly Gln Gly Thr Leu
            100                 105                 110

Val Thr Val Ser Ser
        115

<210> SEQ ID NO 20
<211> LENGTH: 117
<212> TYPE: PRT
<213> ORGANISM: Artificial Sequence
<220> FEATURE:
<223> OTHER INFORMATION: 71H8-VH0

<400> SEQUENCE: 20

Gln Val Gln Leu Val Gln Ser Gly Ala Glu Val Lys Lys Pro Gly Ala
1               5                   10                  15

Ser Val Lys Val Ser Cys Lys Val Ser Gly Asp Thr Phe Thr Ser Tyr
```

```
                   20                  25                  30
Trp Ile Thr Trp Val Arg Gln Ala Pro Gly Lys Gly Leu Glu Trp Met
            35                  40                  45
Gly Asp Ile Tyr Pro Gly Ser Gly Ser Thr Asn Gln Asn Glu Lys Phe
 50                  55                  60
Lys Ser Arg Val Thr Met Thr Glu Asp Thr Ser Asp Thr Ala Tyr
 65                  70                  75                  80
Met Glu Leu Ser Ser Leu Arg Ser Glu Asp Thr Ala Val Tyr Tyr Cys
                85                  90                  95
Ala Thr Leu Arg Pro Tyr Tyr Phe Val Tyr Trp Gly Gln Gly Thr Leu
                100                 105                 110
Val Thr Val Ser Ser
        115

<210> SEQ ID NO 21
<211> LENGTH: 117
<212> TYPE: PRT
<213> ORGANISM: Artificial Sequence
<220> FEATURE:
<223> OTHER INFORMATION: 71H8-VH2

<400> SEQUENCE: 21

Gln Val Gln Leu Val Gln Ser Gly Ala Glu Val Lys Lys Pro Gly Ala
 1               5                  10                  15
Ser Val Lys Val Ser Cys Lys Val Ser Gly Tyr Thr Phe Thr Ser Tyr
                20                  25                  30
Trp Ile Thr Trp Val Arg Gln Arg Pro Gly Lys Gly Leu Glu Trp Met
            35                  40                  45
Gly Asp Ile Tyr Pro Gly Ser Gly Ser Thr Asn Gln Asn Glu Lys Phe
 50                  55                  60
Lys Ser Arg Val Thr Met Thr Val Asp Thr Ser Asp Thr Ala Tyr
 65                  70                  75                  80
Met Glu Leu Ser Ser Leu Arg Ser Glu Asp Thr Ala Val Tyr Tyr Cys
                85                  90                  95
Ala Thr Leu Arg Pro Tyr Tyr Phe Val Tyr Trp Gly Gln Gly Thr Leu
                100                 105                 110
Val Thr Val Ser Ser
        115

<210> SEQ ID NO 22
<211> LENGTH: 117
<212> TYPE: PRT
<213> ORGANISM: Artificial Sequence
<220> FEATURE:
<223> OTHER INFORMATION: 71H8-VH3

<400> SEQUENCE: 22

Gln Val Gln Leu Val Gln Ser Gly Ala Glu Val Lys Lys Pro Gly Ala
 1               5                  10                  15
Ser Val Lys Val Ser Cys Lys Val Ser Gly Tyr Thr Phe Thr Ser Tyr
                20                  25                  30
Trp Ile Thr Trp Val Arg Gln Arg Pro Gly Gln Gly Leu Glu Trp Ile
            35                  40                  45
Gly Asp Ile Tyr Pro Gly Ser Gly Ser Thr Asn Gln Asn Glu Lys Phe
 50                  55                  60
Lys Ser Arg Val Thr Leu Thr Val Asp Thr Ser Asp Thr Ala Tyr
 65                  70                  75                  80
```

```
Met Glu Leu Ser Ser Leu Arg Ser Glu Asp Thr Ala Val Tyr Tyr Cys
             85                  90                  95

Ala Thr Leu Arg Pro Tyr Tyr Phe Val Tyr Trp Gly Gln Gly Thr Leu
            100                 105                 110

Val Thr Val Ser Ser
            115
```

<210> SEQ ID NO 23
<211> LENGTH: 107
<212> TYPE: PRT
<213> ORGANISM: Artificial Sequence
<220> FEATURE:
<223> OTHER INFORMATION: 71H8-VL

<400> SEQUENCE: 23

```
Asp Ile Gln Met Thr Gln Thr Pro Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu Leu Ser Gly Val Pro Ser Arg Phe Ser Gly
50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Leu
                85                  90                  95

Thr Phe Gly Ala Gly Thr Lys Leu Glu Leu Lys
            100                 105
```

<210> SEQ ID NO 24
<211> LENGTH: 107
<212> TYPE: PRT
<213> ORGANISM: Artificial Sequence
<220> FEATURE:
<223> OTHER INFORMATION: 68C8-VL

<400> SEQUENCE: 24

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu Leu Ser Gly Val Pro Ser Arg Phe Ser Gly
50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Leu
                85                  90                  95

Thr Phe Gly Ala Gly Thr Arg Leu Glu Leu Lys
            100                 105
```

<210> SEQ ID NO 25
<211> LENGTH: 112
<212> TYPE: PRT
<213> ORGANISM: Artificial Sequence
<220> FEATURE:
<223> OTHER INFORMATION: 6A12-VL

<400> SEQUENCE: 25

Asp Ile Val Met Thr Gln Thr Pro Phe Ser Asn Pro Val Thr Leu Gly
1               5                   10                  15

Thr Ser Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Asn
                85                  90                  95

Leu Glu Leu Pro Trp Thr Phe Gly Gly Gly Thr Lys Leu Glu Ile Lys
            100                 105                 110

<210> SEQ ID NO 26
<211> LENGTH: 107
<212> TYPE: PRT
<213> ORGANISM: Artificial Sequence
<220> FEATURE:
<223> OTHER INFORMATION: 68C8, 71H8-LV0

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Leu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Thr Leu Pro Leu
                85                  90                  95

Thr Phe Gly Gln Gly Thr Arg Leu Glu Ile Lys
            100                 105

<210> SEQ ID NO 27
<211> LENGTH: 107
<212> TYPE: PRT
<213> ORGANISM: Artificial Sequence
<220> FEATURE:
<223> OTHER INFORMATION: 68C8, 71H8-VL2

<400> SEQUENCE: 27

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Thr Pro Lys Leu Leu Ile
        35                  40                  45

Tyr Tyr Thr Ser Arg Leu Leu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

```
Glu Asp Phe Ala Thr Tyr Tyr Cys Gln Gln Gly Asn Thr Leu Pro Leu
                85                  90                  95

Thr Phe Gly Gln Gly Thr Arg Leu Glu Ile Lys
            100                 105

<210> SEQ ID NO 28
<211> LENGTH: 107
<212> TYPE: PRT
<213> ORGANISM: Artificial Sequence
<220> FEATURE:
<223> OTHER INFORMATION: 68C8, 71H8-VL3

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Thr Val Lys Leu Leu Ile
        35                  40                  45

Tyr Tyr Thr Ser Arg Leu Leu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Gly Asn Thr Leu Pro Leu
                85                  90                  95

Thr Phe Gly Gln Gly Thr Arg Leu Glu Ile Lys
            100                 105

<210> SEQ ID NO 29
<211> LENGTH: 330
<212> TYPE: PRT
<213> ORGANISM: Artificial Sequence
<220> FEATURE:
<223> OTHER INFORMATION: CH

<400> SEQUENCE: 29

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175
```

```
Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 30
<211> LENGTH: 107
<212> TYPE: PRT
<213> ORGANISM: Artificial Sequence
<220> FEATURE:
<223> OTHER INFORMATION: CL

<400> SEQUENCE: 30

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 31
<211> LENGTH: 834
<212> TYPE: DNA
<213> ORGANISM: Homo sapiens

<400> SEQUENCE: 31
atgtgcgtgg gcgcccgccg cctgggccgc ggcccctgcg ccgccctgct gctgctgggc      60
ctgggcctga gcaccgtgac cggcctgcac tgcgtgggcg acacctaccc cagcaacgac     120
cgctgctgcc acgagtgccg ccccggcaac ggcatggtga ccgctgcag ccgcagccag      180 aacaccgtgt gccgcccctg cggccccggc ttctacaacg acgtggtgag cagcaagccc     240
tgcaagccct gcacctggtg caacctgcgc agcggcagcg agcgcaagca gctgtgcacc     300
```

```
gccacccagg acaccgtgtg ccgctgccgc gccggcaccc agcccctgga cagctacaag      360
cccggcgtgg actgcgcccc ctgcccccccc ggccacttca gccccggcga caaccaggcc      420
tgcaagccct ggaccaactg cacctgggcc ggcaagcaca ccctgcagcc cgccagcaac      480
agcagcgacg ccatctgcga ggaccgcgac ccccccgcca cccagcccca ggagacccag      540 ggccccccg cccgcccat caccgtgcag cccaccgagg cctggccccg caccagccag      600
ggccccagca cccgccccgt ggaggtgccc ggcggccgcg ccgtggccgc catcctgggc      660
ctgggcctgg tgctgggcct gctgggcccc ctggccatcc tgctggccct gtacctgctg      720
cgccgcgacc agcgcctgcc ccccgacgcc cacaagcccc ccggcggcgg cagcttccgc      780
acccccatcc aggaggagca ggccgacgcc cacagcaccc tggccaagat ctaa             834
```

<210> SEQ ID NO 32
<211> LENGTH: 277
<212> TYPE: PRT
<213> ORGANISM: Homo sapiens

<400> SEQUENCE: 32

```
Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
            20                  25                  30

Gly Asp Thr Tyr Pro Ser Asn Asp Arg Cys Cys His Glu Cys Arg Pro
        35                  40                  45

Gly Asn Gly Met Val Ser Arg Cys Ser Arg Ser Gln Asn Thr Val Cys
    50                  55                  60

Arg Pro Cys Gly Pro Gly Phe Tyr Asn Asp Val Val Ser Ser Lys Pro
65                  70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
        115                 120                 125

Pro Pro Gly His Phe Ser Pro Gly Asp Asn Gln Ala Cys Lys Pro Trp
    130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
        195                 200                 205

Val Pro Gly Gly Arg Ala Val Ala Ala Ile Leu Gly Leu Gly Leu Val
    210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                245                 250                 255

Gly Ser Phe Arg Thr Pro Ile Gln Glu Glu Gln Ala Asp Ala His Ser
            260                 265                 270

Thr Leu Ala Lys Ile
```

```
                275

<210> SEQ ID NO 33
<211> LENGTH: 834
<212> TYPE: DNA
<213> ORGANISM: Macaca mulatta

<400> SEQUENCE: 33
atgtgcgtgg gcgcccgccg cctgggccgc ggccctgcg ccgccctgct gctgctgggc    60
ctgggcctga gcaccaccgc caagctgcac tgcgtgggcg acacctaccc cagcaacgac   120
cgctgctgcc aggagtgccg ccccggcaac ggcatggtga ccgctgcaa ccgcagccag    180 aacaccgtgt gccgcccctg cggccccggc ttctacaacg acgtggtgag cgccaagccc   240
tgcaaggcct gcacctggtg caacctgcgc agcggcagcg agcgcaagca gcccctgcacc  300 gccacccagg acaccgtgtg ccgctgccgc gccggcaccc agccctgga cagctacaag    360 cccggcgtgg actgcgcccc ctgccccccc ggccacttca gccccggcga caaccaggcc   420
tgcaagccct ggaccaactg cacctggcc ggcaagcaca ccctgcagcc cgccagcaac    480
agcagcgacg ccatctgcga ggaccgcgac ccccccccca cccagcccca ggagacccag   540 ggccccccg cccgccccac caccgtgcag cccaccgagg cctggccccg caccagccag    600
cgccccagca cccgccccgt ggaggtgccc cgcggccccg ccgtggccgc catcctgggc   660
ctgggcctgg ccctgggcct gctgggcccc ctggccatgc tgctggccct gctgctgctg   720
cgccgcgacc agcgcctgcc ccccgacgcc cccaaggccc ccggcggcgg cagcttccgc   780 accccccatcc aggaggagca ggccgacgcc cacagcgccc tggccaagat ctaa         834

<210> SEQ ID NO 34
<211> LENGTH: 277
<212> TYPE: PRT
<213> ORGANISM: Macaca mulatta

<400> SEQUENCE: 34

Met Cys Val Gly Ala Arg Arg Leu Gly Arg Gly Pro Cys Ala Ala Leu
1               5                   10                  15

Leu Leu Leu Gly Leu Gly Leu Ser Thr Thr Ala Lys Leu His Cys Val
            20                  25                  30

Gly Asp Thr Tyr Pro Ser Asn Asp Arg Cys Cys Gln Glu Cys Arg Pro
        35                  40                  45

Gly Asn Gly Met Val Ser Arg Cys Asn Arg Ser Gln Asn Thr Val Cys
    50                  55                  60

Arg Pro Cys Gly Pro Gly Phe Tyr Asn Asp Val Val Ser Ala Lys Pro
65                  70                  75                  80

Cys Lys Ala Cys Thr Trp Cys Asn Leu Arg Ser Gly Ser Glu Arg Lys
                85                  90                  95

Gln Pro Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
        115                 120                 125

Pro Pro Gly His Phe Ser Pro Gly Asp Asn Gln Ala Cys Lys Pro Trp
    130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Thr Gln Pro
                165                 170                 175
```

```
Gln Glu Thr Gln Gly Pro Pro Ala Arg Pro Thr Thr Val Gln Pro Thr
                180                 185                 190

Glu Ala Trp Pro Arg Thr Ser Gln Arg Pro Ser Thr Arg Pro Val Glu
            195                 200                 205

Val Pro Arg Gly Pro Ala Val Ala Ala Ile Leu Gly Leu Gly Leu Ala
        210                 215                 220

Leu Gly Leu Leu Gly Pro Leu Ala Met Leu Leu Ala Leu Leu Leu Leu
225                 230                 235                 240

Arg Arg Asp Gln Arg Leu Pro Pro Asp Ala Pro Lys Ala Pro Gly Gly
                245                 250                 255

Gly Ser Phe Arg Thr Pro Ile Gln Glu Glu Gln Ala Asp Ala His Ser
            260                 265                 270

Ala Leu Ala Lys Ile
            275

<210> SEQ ID NO 35
<211> LENGTH: 819
<212> TYPE: DNA
<213> ORGANISM: Mus musculus

<400> SEQUENCE: 35
atgtacgtgt gggtgcagca gcccaccgcc ctgctgctgc tgggcctgac cctgggcgtg      60
accgcccgcc gcctgaactg cgtgaagcac acctacccca gcggccacaa gtgctgccgc     120
gagtgccagc ccggccacgg catggtgagc cgctgcgacc acacccgcga caccctgtgc     180
caccctgcg agaccggctt ctacaacgag gccgtgaact acgacacctg caagcagtgc     240
acccagtgca accaccgcag cggcagcgag ctgaagcaga actgcacccc cacccaggac     300
accgtgtgcc gctgccgcc cggcacccag ccccgccagg acagcggcta caagctgggc     360
gtggactgcg tgccctgccc ccccggccac ttcagccccg caacaaccca ggcctgcaag     420
ccctggacca actgcaccct gagcggcaag cagacccgcc accccgccag cgacagcctg     480
gacgccgtgt gcgaggaccg cagcctgctg gccaccctgc tgtgggagac ccagcgcccc     540
accttccgcc ccaccaccgt gcagagcacc accgtgtggc ccgcaccag cgagctgccc     600
agccccccca ccctggtgac ccccgagggc cccgccttcg ccgtgctgct gggcctgggc     660
ctgggcctgc tggccccccct gaccgtgctg ctggccctgt acctgctgcg caaggcctgg     720
cgcctgccca cacccccaa gccctgctgg ggcaacagct ccgcaccccc catccaggag     780
gagcacaccg acgcccactt caccctggcc aagatctaa                            819

<210> SEQ ID NO 36
<211> LENGTH: 272
<212> TYPE: PRT
<213> ORGANISM: Mus musculus

<400> SEQUENCE: 36

Met Tyr Val Trp Val Gln Gln Pro Thr Ala Leu Leu Leu Leu Gly Leu
1               5                   10                  15

Thr Leu Gly Val Thr Ala Arg Arg Leu Asn Cys Val Lys His Thr Tyr
            20                  25                  30

Pro Ser Gly His Lys Cys Cys Arg Glu Cys Gln Pro Gly His Gly Met
        35                  40                  45

Val Ser Arg Cys Asp His Thr Arg Asp Thr Leu Cys His Pro Cys Glu
    50                  55                  60

Thr Gly Phe Tyr Asn Glu Ala Val Asn Tyr Asp Thr Cys Lys Gln Cys
65                  70                  75                  80
```

```
Thr Gln Cys Asn His Arg Ser Gly Ser Glu Leu Lys Gln Asn Cys Thr
                85                  90                  95
Pro Thr Gln Asp Thr Val Cys Arg Cys Arg Pro Gly Thr Gln Pro Arg
            100                 105                 110
Gln Asp Ser Gly Tyr Lys Leu Gly Val Asp Cys Val Pro Cys Pro Pro
        115                 120                 125
Gly His Phe Ser Pro Gly Asn Asn Gln Ala Cys Lys Pro Trp Thr Asn
    130                 135                 140
Cys Thr Leu Ser Gly Lys Gln Thr Arg His Pro Ala Ser Asp Ser Leu
145                 150                 155                 160
Asp Ala Val Cys Glu Asp Arg Ser Leu Leu Ala Thr Leu Leu Trp Glu
                165                 170                 175
Thr Gln Arg Pro Thr Phe Arg Pro Thr Thr Val Gln Ser Thr Thr Val
            180                 185                 190
Trp Pro Arg Thr Ser Glu Leu Pro Ser Pro Pro Thr Leu Val Thr Pro
        195                 200                 205
Glu Gly Pro Ala Phe Ala Val Leu Leu Gly Leu Gly Leu Gly Leu Leu
    210                 215                 220
Ala Pro Leu Thr Val Leu Leu Ala Leu Tyr Leu Leu Arg Lys Ala Trp
225                 230                 235                 240
Arg Leu Pro Asn Thr Pro Lys Pro Cys Trp Gly Asn Ser Phe Arg Thr
                245                 250                 255
Pro Ile Gln Glu Glu His Thr Asp Ala His Phe Thr Leu Ala Lys Ile
            260                 265                 270

<210> SEQ ID NO 37
<211> LENGTH: 294
<212> TYPE: PRT
<213> ORGANISM: Artificial Sequence
<220> FEATURE:
<223> OTHER INFORMATION: human OX40-CD40 fusion protein

<400> SEQUENCE: 37

Met Cys Val Gly Ala Arg Arg Leu Gly Arg Gly Pro Cys Ala Ala Leu
1               5                   10                  15
Leu Leu Leu Gly Leu Gly Leu Ser Thr Val Thr Gly Leu His Cys Val
            20                  25                  30
Gly Asp Thr Tyr Pro Ser Asn Asp Arg Cys Cys His Glu Cys Arg Pro
        35                  40                  45
Gly Asn Gly Met Val Ser Arg Cys Ser Arg Ser Gln Asn Thr Val Cys
    50                  55                  60
Arg Pro Cys Gly Pro Gly Phe Tyr Asn Asp Val Val Ser Ser Lys Pro
65                  70                  75                  80
Cys Lys Pro Cys Thr Trp Cys Asn Leu Arg Ser Gly Ser Glu Arg Lys
                85                  90                  95
Gln Leu Cys Thr Ala Thr Gln Asp Thr Val Cys Arg Cys Arg Ala Gly
            100                 105                 110
Thr Gln Pro Leu Asp Ser Tyr Lys Pro Gly Val Asp Cys Ala Pro Cys
        115                 120                 125
Pro Pro Gly His Phe Ser Pro Gly Asp Asn Gln Ala Cys Lys Pro Trp
    130                 135                 140
Thr Asn Cys Thr Leu Ala Gly Lys His Thr Leu Gln Pro Ala Ser Asn
145                 150                 155                 160
Ser Ser Asp Ala Ile Cys Glu Asp Arg Asp Pro Pro Ala Thr Gln Pro
                165                 170                 175
```

```
Gln Glu Thr Gln Gly Pro Pro Ala Arg Pro Ile Thr Val Gln Pro Thr
                180                 185                 190

Glu Ala Trp Pro Arg Thr Ser Gln Gly Pro Ser Thr Arg Pro Val Glu
            195                 200                 205

Val Pro Gly Gly Arg Ala Ala Leu Val Val Ile Pro Ile Ile Phe Gly
210                 215                 220

Ile Leu Phe Ala Ile Leu Leu Val Leu Val Phe Ile Lys Lys Val Ala
225                 230                 235                 240

Lys Lys Pro Thr Asn Lys Ala Pro His Pro Lys Gln Glu Pro Gln Glu
                245                 250                 255

Ile Asn Phe Pro Asp Asp Leu Pro Gly Ser Asn Thr Ala Ala Pro Val
                260                 265                 270

Gln Glu Thr Leu His Gly Cys Gln Pro Val Thr Gln Glu Asp Gly Lys
                275                 280                 285

Glu Ser Arg Ile Ser Val
    290

<210> SEQ ID NO 38
<211> LENGTH: 529
<212> TYPE: PRT
<213> ORGANISM: Artificial Sequence
<220> FEATURE:
<223> OTHER INFORMATION: full length OX40-ECD

<400> SEQUENCE: 38

Met Gly Trp Ser Cys Ile Ile Leu Phe Leu Val Ala Thr Ala Thr Gly
1               5                   10                  15

Val His Ser Leu His Cys Val Gly Asp Thr Tyr Pro Ser Asn Asp Arg
                20                  25                  30

Cys Cys His Glu Cys Arg Pro Gly Asn Gly Met Val Ser Arg Cys Ser
            35                  40                  45

Arg Ser Gln Asn Thr Val Cys Arg Pro Cys Gly Pro Gly Phe Tyr Asn
        50                  55                  60

Asp Val Val Ser Ser Lys Pro Cys Lys Pro Cys Thr Trp Cys Asn Leu
65                  70                  75                  80

Arg Ser Gly Ser Glu Arg Lys Gln Leu Cys Thr Ala Thr Gln Asp Thr
                85                  90                  95

Val Cys Arg Cys Arg Ala Gly Thr Gln Pro Leu Asp Ser Tyr Lys Pro
            100                 105                 110

Gly Val Asp Cys Ala Pro Cys Pro Pro Gly His Phe Ser Pro Gly Asp
        115                 120                 125

Asn Gln Ala Cys Lys Pro Trp Thr Asn Cys Thr Leu Ala Gly Lys His
130                 135                 140

Thr Leu Gln Pro Ala Ser Asn Ser Ser Asp Ala Ile Cys Glu Asp Arg
145                 150                 155                 160

Asp Pro Pro Ala Thr Gln Pro Gln Glu Thr Gln Gly Pro Pro Ala Arg
                165                 170                 175

Pro Ile Thr Val Gln Pro Thr Glu Ala Trp Pro Arg Thr Ser Gln Gly
            180                 185                 190

Pro Ser Thr Arg Pro Val Glu Val Pro Gly Gly Arg Ala Ala Lys Thr
        195                 200                 205

Thr Pro Pro Ser Val Tyr Pro Leu Ala Pro Gly Ser Ala Ala Gln Thr
    210                 215                 220

Asn Ser Met Val Thr Leu Gly Cys Leu Val Lys Gly Tyr Phe Pro Glu
225                 230                 235                 240
```

```
Pro Val Thr Val Thr Trp Asn Ser Gly Ser Leu Ser Ser Gly Val His
            245                 250                 255
Thr Phe Pro Ala Val Leu Gln Ser Asp Leu Tyr Thr Leu Ser Ser Ser
        260                 265                 270
Val Thr Val Pro Ser Ser Thr Trp Pro Ser Glu Thr Val Thr Cys Asn
    275                 280                 285
Val Ala His Pro Ala Ser Ser Thr Lys Val Asp Lys Lys Ile Val Pro
290                 295                 300
Arg Asp Cys Gly Cys Lys Pro Cys Ile Cys Thr Val Pro Glu Val Ser
305                 310                 315                 320
Ser Val Phe Ile Phe Pro Pro Lys Pro Lys Asp Val Leu Thr Ile Thr
                325                 330                 335
Leu Thr Pro Lys Val Thr Cys Val Val Val Asp Ile Ser Lys Asp Asp
            340                 345                 350
Pro Glu Val Gln Phe Ser Trp Phe Val Asp Asp Val Glu Val His Thr
        355                 360                 365
Ala Gln Thr Gln Pro Arg Glu Glu Gln Phe Asn Ser Thr Phe Arg Ser
    370                 375                 380
Val Ser Glu Leu Pro Ile Met His Gln Asp Trp Leu Asn Gly Lys Glu
385                 390                 395                 400
Phe Lys Cys Arg Val Asn Ser Ala Ala Phe Pro Ala Pro Ile Glu Lys
                405                 410                 415
Thr Ile Ser Lys Thr Lys Gly Arg Pro Lys Ala Pro Gln Val Tyr Thr
            420                 425                 430
Ile Pro Pro Pro Lys Glu Gln Met Ala Lys Asp Lys Val Ser Leu Thr
        435                 440                 445
Cys Met Ile Thr Asp Phe Phe Pro Glu Asp Ile Thr Val Glu Trp Gln
    450                 455                 460
Trp Asn Gly Gln Pro Ala Glu Asn Tyr Lys Asn Thr Gln Pro Ile Met
465                 470                 475                 480
Asp Thr Asp Gly Ser Tyr Phe Val Tyr Ser Lys Leu Asn Val Gln Lys
                485                 490                 495
Ser Asn Trp Glu Ala Gly Asn Thr Phe Thr Cys Ser Val Leu His Glu
            500                 505                 510
Gly Leu His Asn His His Thr Glu Lys Ser Leu Ser His Ser Pro Gly
        515                 520                 525
Lys

<210> SEQ ID NO 39
<211> LENGTH: 492
<212> TYPE: PRT
<213> ORGANISM: Artificial Sequence
<220> FEATURE:
<223> OTHER INFORMATION: OX40 truncant 1-mFc

<400> SEQUENCE: 39

Met Gly Trp Ser Cys Ile Ile Leu Phe Leu Val Ala Thr Ala Thr Gly
1               5                   10                  15
Val His Ser Pro Cys Gly Pro Gly Phe Tyr Asn Asp Val Val Ser Ser
            20                  25                  30
Lys Pro Cys Lys Pro Cys Thr Trp Cys Asn Leu Arg Ser Gly Ser Glu
        35                  40                  45
Arg Lys Gln Leu Cys Thr Ala Thr Gln Asp Thr Val Cys Arg Cys Arg
    50                  55                  60
```

```
Ala Gly Thr Gln Pro Leu Asp Ser Tyr Lys Pro Gly Val Asp Cys Ala
 65                  70                  75                  80

Pro Cys Pro Pro Gly His Phe Ser Pro Gly Asp Asn Gln Ala Cys Lys
             85                  90                  95

Pro Trp Thr Asn Cys Thr Leu Ala Gly Lys His Thr Leu Gln Pro Ala
            100                 105                 110

Ser Asn Ser Ser Asp Ala Ile Cys Glu Asp Arg Asp Pro Pro Ala Thr
        115                 120                 125

Gln Pro Gln Glu Thr Gln Gly Pro Pro Ala Arg Pro Ile Thr Val Gln
    130                 135                 140

Pro Thr Glu Ala Trp Pro Arg Thr Ser Gln Gly Pro Ser Thr Arg Pro
145                 150                 155                 160

Val Glu Val Pro Gly Gly Arg Ala Ala Lys Thr Thr Pro Pro Ser Val
                165                 170                 175

Tyr Pro Leu Ala Pro Gly Ser Ala Ala Gln Thr Asn Ser Met Val Thr
            180                 185                 190

Leu Gly Cys Leu Val Lys Gly Tyr Phe Pro Glu Pro Val Thr Val Thr
        195                 200                 205

Trp Asn Ser Gly Ser Leu Ser Ser Gly Val His Thr Phe Pro Ala Val
    210                 215                 220

Leu Gln Ser Asp Leu Tyr Thr Leu Ser Ser Val Thr Val Pro Ser
225                 230                 235                 240

Ser Thr Trp Pro Ser Glu Thr Val Thr Cys Asn Val Ala His Pro Ala
                245                 250                 255

Ser Ser Thr Lys Val Asp Lys Lys Ile Val Pro Arg Asp Cys Gly Cys
            260                 265                 270

Lys Pro Cys Ile Cys Thr Val Pro Glu Val Ser Ser Val Phe Ile Phe
        275                 280                 285

Pro Pro Lys Pro Lys Asp Val Leu Thr Ile Thr Leu Thr Pro Lys Val
    290                 295                 300

Thr Cys Val Val Val Asp Ile Ser Lys Asp Asp Pro Glu Val Gln Phe
305                 310                 315                 320

Ser Trp Phe Val Asp Asp Val Glu Val His Thr Ala Gln Thr Gln Pro
                325                 330                 335

Arg Glu Glu Gln Phe Asn Ser Thr Phe Arg Ser Val Ser Glu Leu Pro
            340                 345                 350

Ile Met His Gln Asp Trp Leu Asn Gly Lys Glu Phe Lys Cys Arg Val
        355                 360                 365

Asn Ser Ala Ala Phe Pro Ala Pro Ile Glu Lys Thr Ile Ser Lys Thr
    370                 375                 380

Lys Gly Arg Pro Lys Ala Pro Gln Val Tyr Thr Ile Pro Pro Pro Lys
385                 390                 395                 400

Glu Gln Met Ala Lys Asp Lys Val Ser Leu Thr Cys Met Ile Thr Asp
                405                 410                 415

Phe Phe Pro Glu Asp Ile Thr Val Glu Trp Gln Trp Asn Gly Gln Pro
            420                 425                 430

Ala Glu Asn Tyr Lys Asn Thr Gln Pro Ile Met Asp Thr Asp Gly Ser
        435                 440                 445

Tyr Phe Val Tyr Ser Lys Leu Asn Val Gln Lys Ser Asn Trp Glu Ala
    450                 455                 460

Gly Asn Thr Phe Thr Cys Ser Val Leu His Glu Gly Leu His Asn His
465                 470                 475                 480

His Thr Glu Lys Ser Leu Ser His Ser Pro Gly Lys
```

<210> SEQ ID NO 40
<211> LENGTH: 450
<212> TYPE: PRT
<213> ORGANISM: Artificial Sequence
<220> FEATURE:
<223> OTHER INFORMATION: OX40 truncant 2-mFc

<400> SEQUENCE: 40

```
Met Gly Trp Ser Cys Ile Ile Leu Phe Leu Val Ala Thr Ala Thr Gly
1               5                   10                  15

Val His Ser Arg Cys Arg Ala Gly Thr Gln Pro Leu Asp Ser Tyr Lys
            20                  25                  30

Pro Gly Val Asp Cys Ala Pro Cys Pro Pro Gly His Phe Ser Pro Gly
        35                  40                  45

Asp Asn Gln Ala Cys Lys Pro Trp Thr Asn Cys Thr Leu Ala Gly Lys
    50                  55                  60

His Thr Leu Gln Pro Ala Ser Asn Ser Ser Asp Ala Ile Cys Glu Asp
65                  70                  75                  80

Arg Asp Pro Pro Ala Thr Gln Pro Gln Glu Thr Gln Gly Pro Pro Ala
                85                  90                  95

Arg Pro Ile Thr Val Gln Pro Thr Glu Ala Trp Pro Arg Thr Ser Gln
            100                 105                 110

Gly Pro Ser Thr Arg Pro Val Glu Val Pro Gly Gly Arg Ala Ala Lys
        115                 120                 125

Thr Thr Pro Pro Ser Val Tyr Pro Leu Ala Pro Gly Ser Ala Ala Gln
    130                 135                 140

Thr Asn Ser Met Val Thr Leu Gly Cys Leu Val Lys Gly Tyr Phe Pro
145                 150                 155                 160

Glu Pro Val Thr Val Thr Trp Asn Ser Gly Ser Leu Ser Ser Gly Val
                165                 170                 175

His Thr Phe Pro Ala Val Leu Gln Ser Asp Leu Tyr Thr Leu Ser Ser
            180                 185                 190

Ser Val Thr Val Pro Ser Ser Thr Trp Pro Ser Glu Thr Val Thr Cys
        195                 200                 205

Asn Val Ala His Pro Ala Ser Ser Thr Lys Val Asp Lys Lys Ile Val
    210                 215                 220

Pro Arg Asp Cys Gly Cys Lys Pro Cys Ile Cys Thr Val Pro Glu Val
225                 230                 235                 240

Ser Ser Val Phe Ile Phe Pro Pro Lys Pro Lys Asp Val Leu Thr Ile
                245                 250                 255

Thr Leu Thr Pro Lys Val Thr Cys Val Val Val Asp Ile Ser Lys Asp
            260                 265                 270

Asp Pro Glu Val Gln Phe Ser Trp Phe Val Asp Asp Val Glu Val His
        275                 280                 285

Thr Ala Gln Thr Gln Pro Arg Glu Glu Gln Phe Asn Ser Thr Phe Arg
    290                 295                 300

Ser Val Ser Glu Leu Pro Ile Met His Gln Asp Trp Leu Asn Gly Lys
305                 310                 315                 320

Glu Phe Lys Cys Arg Val Asn Ser Ala Ala Phe Pro Ala Pro Ile Glu
                325                 330                 335

Lys Thr Ile Ser Lys Thr Lys Gly Arg Pro Lys Ala Pro Gln Val Tyr
            340                 345                 350

Thr Ile Pro Pro Pro Lys Glu Gln Met Ala Lys Asp Lys Val Ser Leu
```

```
                355                 360                 365
Thr Cys Met Ile Thr Asp Phe Phe Pro Glu Asp Ile Thr Val Glu Trp
    370                 375                 380

Gln Trp Asn Gly Gln Pro Ala Glu Asn Tyr Lys Asn Thr Gln Pro Ile
385                 390                 395                 400

Met Asp Thr Asp Gly Ser Tyr Phe Val Tyr Ser Lys Leu Asn Val Gln
                405                 410                 415

Lys Ser Asn Trp Glu Ala Gly Asn Thr Phe Thr Cys Ser Val Leu His
            420                 425                 430

Glu Gly Leu His Asn His His Thr Glu Lys Ser Leu Ser His Ser Pro
        435                 440                 445

Gly Lys
    450

<210> SEQ ID NO 41
<211> LENGTH: 431
<212> TYPE: PRT
<213> ORGANISM: Artificial Sequence
<220> FEATURE:
<223> OTHER INFORMATION: OX40 truncant 3-mFc

<400> SEQUENCE: 41

Met Gly Trp Ser Cys Ile Ile Leu Phe Leu Val Ala Thr Ala Thr Gly
1               5                   10                  15

Val His Ser Pro Cys Pro Gly His Phe Ser Pro Gly Asp Asn Gln
            20                  25                  30

Ala Cys Lys Pro Trp Thr Asn Cys Thr Leu Ala Gly Lys His Thr Leu
        35                  40                  45

Gln Pro Ala Ser Asn Ser Ser Asp Ala Ile Cys Glu Asp Arg Asp Pro
    50                  55                  60

Pro Ala Thr Gln Pro Gln Glu Thr Gln Gly Pro Pro Ala Arg Pro Ile
65                  70                  75                  80

Thr Val Gln Pro Thr Glu Ala Trp Pro Arg Thr Ser Gln Gly Pro Ser
                85                  90                  95

Thr Arg Pro Val Glu Val Pro Gly Gly Arg Ala Ala Lys Thr Thr Pro
            100                 105                 110

Pro Ser Val Tyr Pro Leu Ala Pro Gly Ser Ala Ala Gln Thr Asn Ser
        115                 120                 125

Met Val Thr Leu Gly Cys Leu Val Lys Gly Tyr Phe Pro Glu Pro Val
    130                 135                 140

Thr Val Thr Trp Asn Ser Gly Ser Leu Ser Ser Gly Val His Thr Phe
145                 150                 155                 160

Pro Ala Val Leu Gln Ser Asp Leu Tyr Thr Leu Ser Ser Ser Val Thr
                165                 170                 175

Val Pro Ser Ser Thr Trp Pro Ser Glu Thr Val Thr Cys Asn Val Ala
            180                 185                 190

His Pro Ala Ser Ser Thr Lys Val Asp Lys Lys Ile Val Pro Arg Asp
        195                 200                 205

Cys Gly Cys Lys Pro Cys Ile Cys Thr Val Pro Glu Val Ser Ser Val
    210                 215                 220

Phe Ile Phe Pro Pro Lys Pro Lys Asp Val Leu Thr Ile Thr Leu Thr
225                 230                 235                 240

Pro Lys Val Thr Cys Val Val Val Asp Ile Ser Lys Asp Asp Pro Glu
                245                 250                 255

Val Gln Phe Ser Trp Phe Val Asp Asp Val Glu Val His Thr Ala Gln
```

```
                260                 265                 270
Thr Gln Pro Arg Glu Glu Gln Phe Asn Ser Thr Phe Arg Ser Val Ser
        275                 280                 285

Glu Leu Pro Ile Met His Gln Asp Trp Leu Asn Gly Lys Glu Phe Lys
        290                 295                 300

Cys Arg Val Asn Ser Ala Ala Phe Pro Ala Pro Ile Glu Lys Thr Ile
305                 310                 315                 320

Ser Lys Thr Lys Gly Arg Pro Lys Ala Pro Gln Val Tyr Thr Ile Pro
                325                 330                 335

Pro Pro Lys Glu Gln Met Ala Lys Asp Lys Val Ser Leu Thr Cys Met
                340                 345                 350

Ile Thr Asp Phe Phe Pro Glu Asp Ile Thr Val Glu Trp Gln Trp Asn
                355                 360                 365

Gly Gln Pro Ala Glu Asn Tyr Lys Asn Thr Gln Pro Ile Met Asp Thr
        370                 375                 380

Asp Gly Ser Tyr Phe Val Tyr Ser Lys Leu Asn Val Gln Lys Ser Asn
385                 390                 395                 400

Trp Glu Ala Gly Asn Thr Phe Thr Cys Ser Val Leu His Glu Gly Leu
                405                 410                 415

His Asn His His Thr Glu Lys Ser Leu Ser His Ser Pro Gly Lys
                420                 425                 430
```

<210> SEQ ID NO 42
<211> LENGTH: 19
<212> TYPE: PRT
<213> ORGANISM: Artificial Sequence
<220> FEATURE:
<223> OTHER INFORMATION: signal peptide

<400> SEQUENCE: 42

```
Met Gly Trp Ser Cys Ile Ile Leu Phe Leu Val Ala Thr Ala Thr Gly
1               5                   10                  15

Val His Ser
```

<210> SEQ ID NO 43
<211> LENGTH: 324
<212> TYPE: PRT
<213> ORGANISM: Artificial Sequence
<220> FEATURE:
<223> OTHER INFORMATION: mFc-tag

<400> SEQUENCE: 43

```
Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
        20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
        50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
```

```
                    115                 120                 125
Thr Ile Thr Leu Thr Pro Lys Val Thr Cys Val Val Val Asp Ile Ser
        130                 135                 140

Lys Asp Asp Pro Glu Val Gln Phe Ser Trp Phe Val Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
                180                 185                 190

Gly Lys Glu Phe Lys Cys Arg Val Asn Ser Ala Ala Phe Pro Ala Pro
                195                 200                 205

Ile Glu Lys Thr Ile Ser Lys Thr Lys Gly Arg Pro Lys Ala Pro Gln
        210                 215                 220

Val Tyr Thr Ile Pro Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
                260                 265                 270

Pro Ile Met Asp Thr Asp Gly Ser Tyr Phe Val Tyr Ser Lys Leu Asn
        275                 280                 285

Val Gln Lys Ser Asn Trp Glu Ala Gly Asn Thr Phe Thr Cys Ser Val
        290                 295                 300

Leu His Glu Gly Leu His Asn His His Thr Glu Lys Ser Leu Ser His
305                 310                 315                 320

Ser Pro Gly Lys
```